(12) United States Patent
Kato

(10) Patent No.: US 10,066,567 B2
(45) Date of Patent: Sep. 4, 2018

(54) CONTROL DEVICE AND CONTROL METHOD OF INTERNAL COMBUSTION ENGINE

(71) Applicant: TOYOTA JIDOSHA KABUSHIKI KAISHA, Toyota-shi, Aichi-ken (JP)

(72) Inventor: Mie Kato, Gotenba (JP)

(73) Assignee: TOYOTA JIDOSHA KABUSHIKI KAISHA, Toyota-shi, Aichi-ken (JP)

( * ) Notice: Subject to any disclaimer, the term of this patent is extended or adjusted under 35 U.S.C. 154(b) by 0 days.

(21) Appl. No.: 15/513,833

(22) PCT Filed: Sep. 21, 2015

(86) PCT No.: PCT/IB2015/001732
§ 371 (c)(1),
(2) Date: Mar. 23, 2017

(87) PCT Pub. No.: WO2016/046624
PCT Pub. Date: Mar. 31, 2016

(65) Prior Publication Data
US 2017/0298853 A1 Oct. 19, 2017

(30) Foreign Application Priority Data

Sep. 26, 2014 (JP) ................. 2014-197595

(51) Int. Cl.
*F01N 3/00* (2006.01)
*F02D 41/14* (2006.01)
(Continued)

(52) U.S. Cl.
CPC ........... *F02D 41/1495* (2013.01); *F01N 3/10* (2013.01); *F01N 11/00* (2013.01); *F02D 41/123* (2013.01);
(Continued)

(58) Field of Classification Search
USPC .......... 60/274, 276, 277, 286, 297, 300, 303
See application file for complete search history.

(56) References Cited

U.S. PATENT DOCUMENTS 5,656,190 A   12/1997 Aoki
6,439,038 B1   8/2002 Rösel et al.
(Continued)

FOREIGN PATENT DOCUMENTS

DE   19733107 A1   2/1999
EP   0994345 A2   4/2000
(Continued)

*Primary Examiner* — Binh Q Tran
(74) *Attorney, Agent, or Firm* — Sughrue Mion, PLLC

(57) ABSTRACT

A control device of an internal combustion engine is configured to perform a fuel cut-off control and an abnormality diagnosis control. A heating device for heating an element of an air-fuel ratio sensor is controlled by making an element temperature of the air-fuel ratio sensor become a target element temperature. The target element temperature of the air-fuel ratio sensor during a high temperature control period from a time when a prescribed high temperature control begins after a start of the internal combustion engine to a time when the prescribed high temperature control is completed after completion of the abnormality diagnosis control of the air-fuel ratio sensor is set to be higher than the target element temperature outside the high temperature control period.

8 Claims, 13 Drawing Sheets

(51) Int. Cl.
*F02D 41/12* (2006.01)
*F01N 3/10* (2006.01)
*F01N 11/00* (2006.01)
*G01M 15/10* (2006.01)
*G01N 27/407* (2006.01)

(52) U.S. Cl.
CPC ....... *F02D 41/1494* (2013.01); *G01M 15/102* (2013.01); *F01N 2550/02* (2013.01); *G01N 27/407* (2013.01)

(56) References Cited

U.S. PATENT DOCUMENTS

| | | | |
|---|---|---|---|
| 8,407,984 B2 * | 4/2013 | Hashimoto | F02D 41/1494 60/274 |
| 2007/0012564 A1 * | 1/2007 | Hayashi | G01N 27/4175 204/401 |
| 2012/0046910 A1 * | 2/2012 | Iwazaki | F02D 41/1454 702/183 |
| 2013/0206596 A1 * | 8/2013 | Katsurahara | G01N 27/407 204/424 |
| 2014/0188371 A1 * | 7/2014 | Miyaji | F02D 41/123 701/103 |
| 2015/0025778 A1 * | 1/2015 | Matsuoka | G01N 27/4065 701/104 |

FOREIGN PATENT DOCUMENTS

| | | |
|---|---|---|
| JP | 08-220059 A | 8/1996 |
| JP | 2000055861 A | 2/2000 |
| JP | 2001074693 A | 3/2001 |
| JP | 2003-148206 A | 5/2003 |
| JP | 2005-002974 A | 1/2005 |
| JP | 2006-177371 A | 7/2006 |
| JP | 2009019558 A | 1/2009 |
| JP | 2009-145235 A | 7/2009 |
| JP | 2009-299545 A | 12/2009 |

* cited by examiner

CONTROL DEVICE AND CONTROL METHOD OF INTERNAL COMBUSTION ENGINE

CROSS REFERENCE TO RELATED APPLICATIONS

This application is a National Stage of International Application No. PCT/IB2015/001732 filed Sep. 21, 2015, claiming priority based on Japanese Patent Application No. 2014-197595 filed Sep. 26, 2014, the contents of all of which are incorporated herein by reference in their entirety.

BACKGROUND OF THE INVENTION

1. Field of the Invention

The invention relates to a control device and a control method of an internal combustion engine.

2. Description of Related Art

In the past, a control device of an internal combustion engine is known, wherein an air-fuel ratio sensor is provided on an exhaust passage of the internal combustion engine, and a fuel amount supplied to the internal combustion engine is controlled based on an output of the air-fuel ratio sensor.

The air-fuel ratio sensor used in such an internal combustion engine includes a case that an abnormality occurs due to deterioration along with its use and the like. When such abnormality occurs in the air-fuel ratio sensor, the fuel amount supplied to the internal combustion engine cannot be properly controlled, and faults will be produced in various controls carried out by the control device of the internal combustion engine. Accordingly, in the control device of the internal combustion engine using such an air-fuel ratio sensor, an abnormality diagnosis control that performs an abnormality diagnosis of the air-fuel ratio sensor is generally carried out.

In a control device described in Japanese Patent Application Publication No. 2009-299545 (JP 2009-299545 A), as such an abnormality diagnosis control, for example, the following control is performed: firstly, switching stepwise an air-fuel ratio of an exhaust gas circulating around the air-fuel ratio sensor from an air-fuel ratio richer than a theoretical air-fuel ratio (hereinafter also referred to as a "rich air-fuel ratio") to an air-fuel ratio leaner than the theoretical air-fuel ratio (hereinafter also referred to as a "lean air-fuel ratio"); then measuring a step response of an output air-fuel ratio of the air-fuel ratio sensor when the air-fuel ratio of the exhaust gas is switched in this manner; similarly, switching stepwise the air-fuel ratio of the exhaust gas circulating around the air-fuel ratio sensor from the lean air-fuel ratio to the rich air-fuel ratio, and measuring the step response of the output air-fuel ratio of the air-fuel ratio sensor at this time; then, calculating parameters of a one-time delay system based on the above measured values, thereby performing the abnormality diagnosis of the air-fuel ratio sensor.

Moreover, an output voltage of the air-fuel ratio sensor has a high temperature dependency, so in the device described in JP 2009-299545 A, an element temperature of the air-fuel ratio sensor is kept as a prescribed activity temperature (e.g., equal to or larger than 600° C.). Thus, a detection accuracy of the air-fuel ratio sensor can be well maintained, and the abnormality diagnosis of the air-fuel ratio sensor can be properly executed.

However, as the abnormality diagnosis control of the air-fuel ratio sensor, for example, an abnormality diagnosis control performed in a fuel cut-off control that temporarily stops a fuel supply to a combustion chamber of the internal combustion engine during an operation of the internal combustion engine is put forward. To be specific, for example, before beginning of the fuel cut-off control, the exhaust gas circulating around the air-fuel ratio sensor is made to have the theoretical air-fuel ratio or the rich air-fuel ratio, and then an atmospheric gas is made to circulate around the air-fuel ratio sensor by beginning the fuel cut-off control. The abnormality diagnosis of the air-fuel ratio sensor is performed based on a responsibility of the air-fuel ratio detected by the air-fuel ratio sensor (hereinafter also referred to as an "output air-fuel ratio") at this time.

In order to accurately perform the abnormality diagnosis of the air-fuel ratio sensor during such a fuel cut-off control, it is required that the air-fuel ratio should be detectable by the air-fuel ratio sensor in an area of a large scope from the rich air-fuel ratio to the lean air-fuel ratio having a large lean degree (atmospheric gas). However, when the element temperature of the air-fuel ratio sensor is low, although the air-fuel ratio near the theoretical air-fuel ratio can be accurately detected, the lean air-fuel ratio having a large lean degree like the atmospheric gas cannot be accurately detected.

On the other hand, when the element temperature of the air-fuel ratio sensor is maintained comparatively high all the time by a heater provided in the air-fuel ratio sensor, electric power consumed by heating by the heater increases. Moreover, in order to decrease the electric power consumed by the heating by the heater, a case that heating of the air-fuel ratio sensor is performed by the heater from the beginning of the fuel cut-off control is also considered. However, when the heating based on the heater is performed in this manner, in many cases, the fuel cut-off control will be completed before a sufficient rise of the element temperature of the air-fuel ratio sensor. Accordingly, in many cases, the lean air-fuel ratio having a large lean degree cannot be accurately detected during the fuel cut-off control, thereby the abnormality diagnosis of the air-fuel ratio sensor cannot be properly performed.

SUMMARY OF THE INVENTION

The object of the invention is to provide a control device and a control method of an internal combustion engine that maintains electric power consumed by a heater for heating an air-fuel ratio sensor comparatively low, and can reliably perform an abnormality diagnosis of the air-fuel ratio sensor by means of an abnormality diagnosis performed during a fuel cut-off control.

A first aspect of the invention relates to a control device of an internal combustion engine, the internal combustion engine having an air-fuel ratio sensor provided on an exhaust passage of the internal combustion engine, the air-fuel ratio sensor having a heating device for heating an element thereof, wherein the control device is configured to carry out a fuel cut-off control and an abnormality diagnosis control, the fuel cut-off control being a control that stops or reduces a fuel supply to a combustion chamber of the internal combustion engine during an operation of the internal combustion engine, and the abnormality diagnosis control being a control that performs an abnormality diagnosis of the air-fuel ratio sensor during the fuel cut-off control or after completion of the fuel cut-off control, the control device controls the heating device by making an element temperature of the air-fuel ratio sensor become a target element temperature, and the target element temperature of the air-fuel ratio sensor during a high temperature control period from a time when a prescribed high temperature control begins after a start of the internal combustion engine to a time when the prescribed high temperature control is completed after completion of the abnormality diagnosis control of the air-fuel ratio sensor is set to be higher than the target element temperature outside the high temperature control period.

A second aspect of the invention is based on the first aspect, wherein the control device begins carrying out the abnormality diagnosis control when conditions for carrying out the abnormality diagnosis including a condition for carrying out the fuel cut-off control are satisfied, and the time when the high temperature control begins is a time when or before the conditions for carrying out the abnormality diagnosis other than the condition for carrying out the fuel cut-off control are satisfied.

A third aspect of the invention is based on the first or second aspect, wherein the target element temperature during the high temperature control period is a temperature at which the air-fuel ratio sensor output a limit current when an atmospheric gas circulates around the air-fuel ratio sensor.

A fourth aspect of the invention is based on any one of the first to third aspects, wherein the air-fuel ratio sensor is a cup-shaped air-fuel ratio sensor.

A fifth aspect of the invention is based on any one of the first to fourth aspects, wherein the air-fuel ratio sensor is a downstream side air-fuel ratio sensor that is provided on a downstream side of an exhaust flow direction of an exhaust purification catalyst provided on the exhaust passage of the internal combustion engine.

A sixth aspect of the invention is based on any one of the first to fifth aspects, wherein the control device is configured to carry out a catalyst abnormality diagnosis control, which is a control that performs an abnormality diagnosis of an exhaust purification catalyst provided on the exhaust passage of the internal combustion engine after the completion of the fuel cut-off control, and in a case where a time when the catalyst abnormality diagnosis control of the exhaust purification catalyst is completed is later than a time when the abnormality diagnosis control of the air-fuel ratio sensor is completed, the time when the high temperature control is completed is a time after the abnormality diagnosis control of the exhaust purification catalyst is completed.

A seventh aspect of the invention is based on any one of the first to sixth aspects, wherein the control device is configured to carry out a catalyst abnormality diagnosis control, which is a control that performs an abnormality diagnosis of an exhaust purification catalyst provided on the exhaust passage of the internal combustion engine after the completion of the fuel cut-off control, the control device performs an after-restoration richness control, which is a control that controls an air-fuel ratio by making an air-fuel ratio of an exhaust gas flowing into the exhaust purification catalyst provided on the exhaust passage of the internal combustion engine become a rich air-fuel ratio richer than a theoretical air-fuel ratio, after the completion of the fuel cut-off control, and the time when the high temperature control is completed is a time when or before the after-restoration richness control is completed.

A eighth aspect of the invention relates to a control method of an internal combustion engine, the internal combustion engine having an air-fuel ratio sensor provided on an exhaust passage of the internal combustion engine, the air-fuel ratio sensor having a heating device for heating an element thereof, wherein a fuel cut-off control and an abnormality diagnosis control are configured to be carried out, the fuel cut-off control being a control that stops or reduces a fuel supply to a combustion chamber of the internal combustion engine during an operation of the internal combustion engine, and the abnormality diagnosis control being a control that performs an abnormality diagnosis of the air-fuel ratio sensor during the fuel cut-off control or after completion of the fuel cut-off control, the heating device is controlled by making an element temperature of the air-fuel ratio sensor become a target element temperature, and the target element temperature of the air-fuel ratio sensor during a high temperature control period from a time when a prescribed high temperature control begins after a start of the internal combustion engine to a time when the prescribed high temperature control is completed after completion of the abnormality diagnosis control of the air-fuel ratio sensor is set to be higher than the target element temperature outside the high temperature control period.

In accordance with the respective aspects of the invention, a control device or a control method of an internal combustion engine is provided, which maintains electric power consumed by a heater for heating an air-fuel ratio sensor comparatively low, and can reliably perform an abnormality diagnosis of the air-fuel ratio sensor by means of an abnormality diagnosis performed during a fuel cut-off control.

BRIEF DESCRIPTION OF THE DRAWINGS

Features, advantages, and technical and industrial significance of exemplary embodiments of the invention will be described below with reference to the accompanying drawings, in which like numerals denote like elements, and wherein.

DETAILED DESCRIPTION OF EMBODIMENTS

Embodiments of the invention are described in detail below with reference to the accompanying drawings. It should be noted that in the descriptions below, a same reference sign is marked with respect to a same component element.

First Embodiment

<Descriptions of a Whole of an Internal Combustion Engine>

Figure 1:
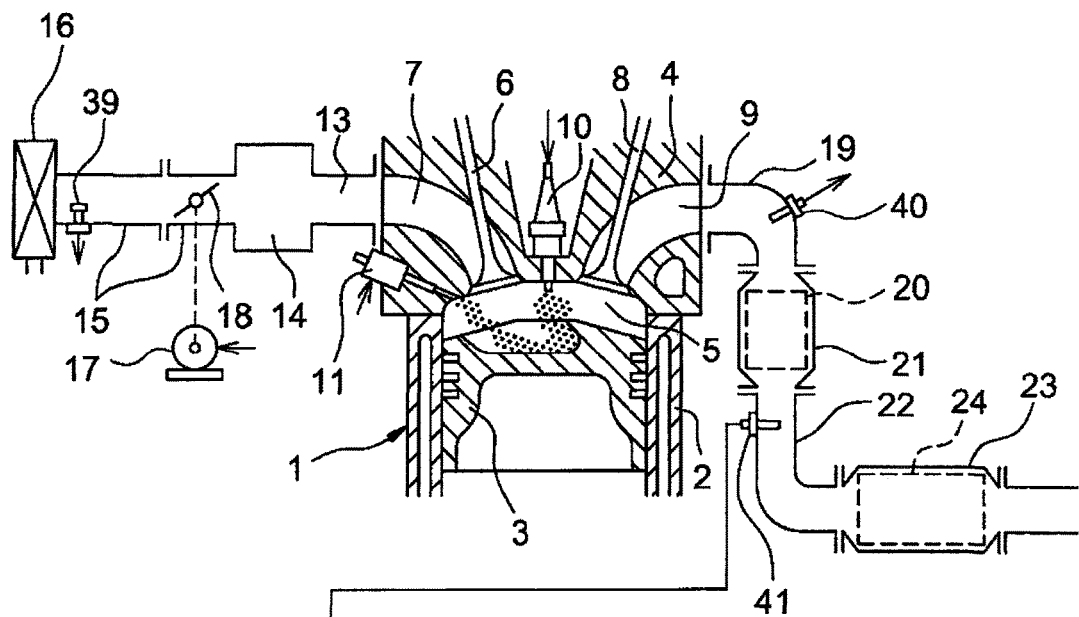
FIG. 1 is a view generally showing an internal combustion engine using a control device according to a first embodiment of the invention.
Figure 1:
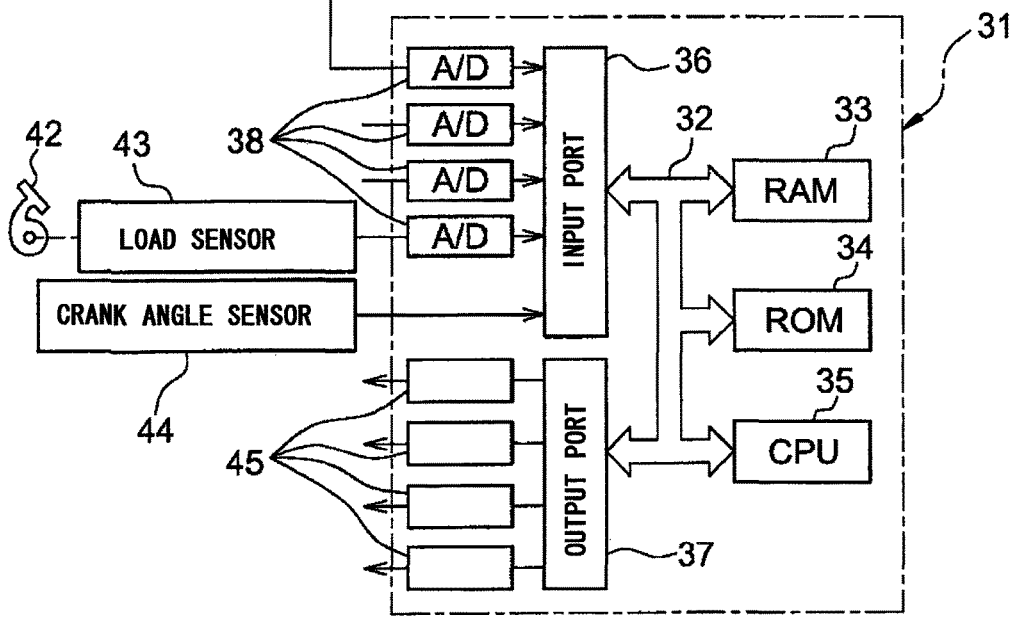

FIG. 1 is a view generally showing an internal combustion engine using a control device according to a first embodiment of the invention. In FIG. 1, an engine body 1, a cylinder block 2, a piston 3 that performs a reciprocating movement within the cylinder block 2, a cylinder head 4 fixed onto the cylinder block 2, a combustion chamber 5 formed between the piston 3 and the cylinder head 4, an intake valve 6, an intake port 7, an exhaust valve 8, and an exhaust port 9 are shown. The intake valve 6 can open and close the intake port 7, and the exhaust valve 8 can open and close the exhaust port 9.

As shown in FIG. 1, a spark plug 10 is provided in a central part of an inner wall surface of the cylinder head 4, and a fuel injection valve 11 is provided in a peripheral part of the inner wall surface of the cylinder head 4. The spark plug 10 is configured to produce sparks in accordance with an ignition signal. Moreover, the fuel injection valve 11 injects a fuel of a specified amount into the combustion chamber 5 in accordance with an injection signal. It should be noted that the fuel injection valve 11 can be configured to inject the fuel into the intake port 7. Moreover, in this embodiment, gasoline having a theoretical air-fuel ratio of 14.6 is used as the fuel. However, other fuels can be also used in an internal combustion engine using a diagnosing device of the invention.

The intake ports 7 of the respective cylinders are respectively connected with a surge tank 14 via the corresponding intake branches 13, and the surge tank 14 is connected with an air cleaner 16 via an intake pipe 15. The intake ports 7, the intake branches 13, the surge tank 14 and the intake pipe 15 form an intake passage. Moreover, a throttle valve 18 driven by a throttle valve drive actuator 17 is provided in the intake pipe 15. The throttle valve 18 is rotated by the throttle valve drive actuator 17, thus an opening area of the intake passage can be changed.

On the other hand, the exhaust ports 9 of the respective cylinders are connected with an exhaust manifold 19. The exhaust manifold 19 has a plurality of branches connected with the respective exhaust ports 9 and a convergence portion at which these branches converge. The convergence portion of the exhaust manifold 19 is connected with an upstream side case 21 in which an upstream side exhaust purification catalyst 20 is provided. The upstream side case 21 is connected with a downstream side case 23 in which a downstream side exhaust purification catalyst 24 is provided, via an exhaust pipe 22. The exhaust ports 9, the exhaust manifold 19, the upstream side case 21, the exhaust pipe 22 and the downstream side case 23 form an exhaust passage.

An electronic control unit (ECU) 31 is formed by a digital computer, and has an RAM (random access memory) 33, an ROM (read-only memory) 34, a CPU (microprocessor) 35, an input port 36 and an output port 37 connected to each other via a bidirectional bus 32. An airflow meter 39 for detecting a flow rate of air flowing in the intake pipe 15 is provided in the intake pipe 15, and an output of the airflow meter 39 is input to the input port 36 via a corresponding AD converter 38. Moreover, an upstream side air-fuel ratio sensor 40 for detecting an air-fuel ratio of an exhaust gas flowing in the exhaust manifold 19 (i.e., an exhaust gas flowing into the upstream side exhaust purification catalyst 20) is provided in the convergence portion of the exhaust manifold 19. Moreover, a downstream side air-fuel ratio sensor 41 for detecting an air-fuel ratio of an exhaust gas flowing in the exhaust pipe 22 (i.e., an exhaust gas flowing out of the upstream side exhaust purification catalyst 20 and flowing into the downstream side exhaust purification catalyst 24) is provided in the exhaust pipe 22. Outputs of the air-fuel ratio sensors 40, 41 are also input to the input port 36 via the respective AD converters 38. It should be noted that the structures of these air-fuel ratio sensors 40, 41 are described later.

Moreover, a load sensor 43 that produces an output voltage in proportion to a operating amount of an accelerator pedal 42 is connected to the accelerator pedal 42, and the output voltage of the load sensor 43 is input to the input port 36 via the corresponding AD converter 38. A crank angle sensor 44 produces an output pulse every time a crank shaft is rotated, for example, by 15 degrees, and the output pulse is input to the input port 36. In the CPU 35, an engine speed is calculated in accordance with the output pulse of the crank angle sensor 44. On the other hand, the output port 37 is connected with the spark plug 10, the fuel injection valve 11 and the throttle valve drive actuator 17 via the respective drive circuits 45. It should be noted that the ECU 31 functions as a control device that controls the internal combustion engine.

The upstream side exhaust purification catalyst 20 and the downstream side exhaust purification catalyst 24 are three-way catalysts having an oxygen absorption capacity. To be specific, the exhaust purification catalyst 20, 24 is a structure that makes a carrier formed by ceramics carry a noble metal having a catalyzing function (e.g., platinum (Pt)) and a substance having an oxygen absorption capacity (e.g., cerium dioxide ($CeO_2$)). The exhaust purification catalyst 20, 24 further plays the oxygen absorption capacity in addition to functioning as a catalyst that simultaneously purifies gases that have not been combusted (HC, CO, etc.) and nitrogen oxide (NOx) when reaching a prescribed activity temperature.

In accordance with the oxygen absorption capacity of the exhaust purification catalyst 20, 24, the exhaust purification catalyst 20, 24 absorbs oxygen in the exhaust gas when the air-fuel ratio of the exhaust gas flowing into the exhaust purification catalyst 20, 24 (hereinafter also referred to as a "lean air-fuel ratio") is leaner than the theoretical air-fuel ratio. On the other hand, the exhaust purification catalyst 20, 24 discharges the oxygen absorbed in the exhaust purification catalyst 20, 24 when the air-fuel ratio of the exhaust gas flowing into the exhaust purification catalyst 20, 24 (hereinafter also referred to as a "rich air-fuel ratio") is richer than the theoretical air-fuel ratio. As a result, as long as the oxygen absorption capacity of the exhaust purification catalyst 20, 24 is maintained, no matter what is the air-fuel ratio of the exhaust gas flowing into the exhaust purification catalyst 20, 24, the air-fuel ratio of the exhaust gas flowing out of the exhaust purification catalyst 20, 24 substantially becomes the theoretical air-fuel ratio.

<Descriptions of an Air-Fuel Ratio Sensor>

Figure 2:
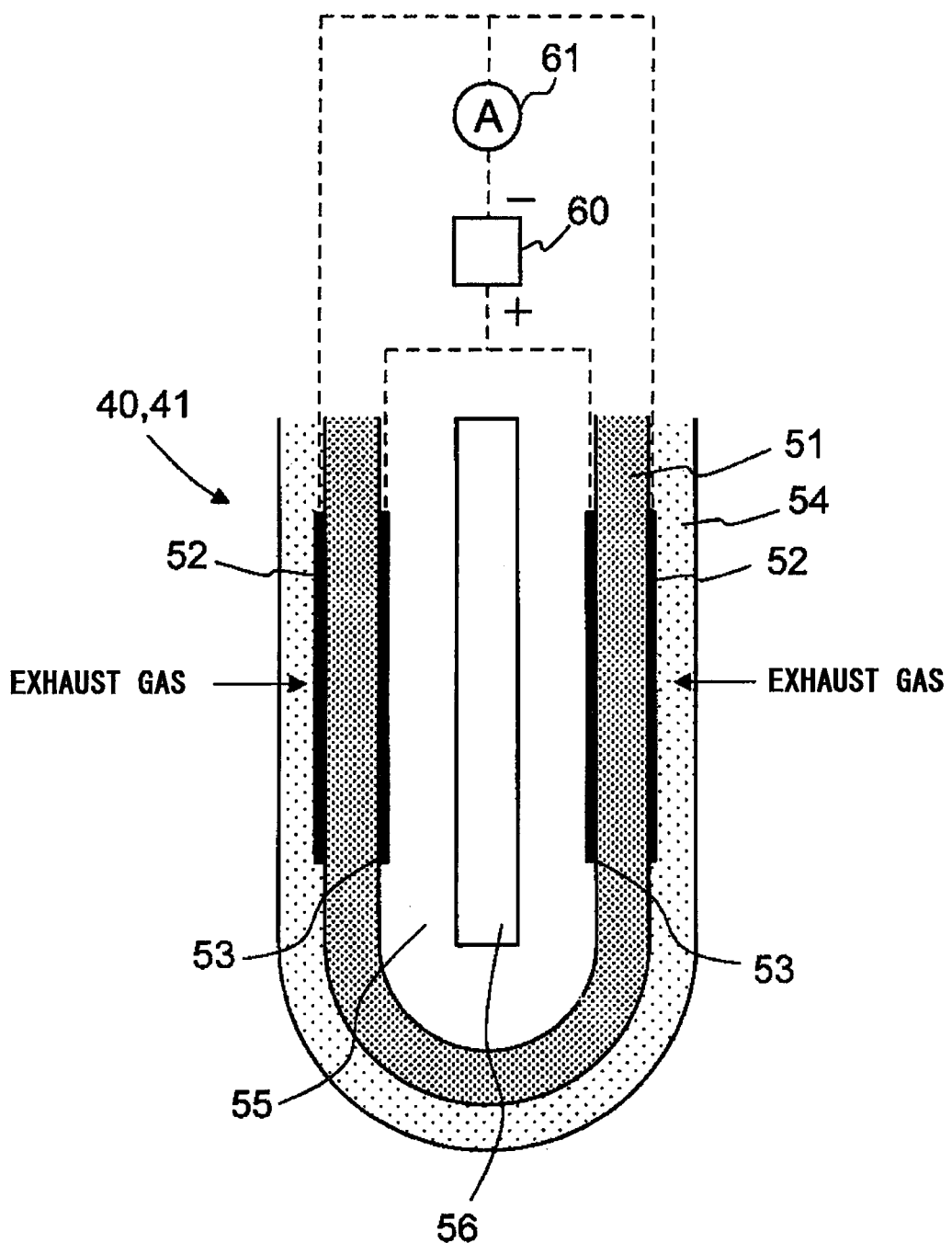
FIG. 2 is a general sectional view of an air-fuel ratio sensor.

In the embodiment, a cup-shaped limit current air-fuel ratio sensor is used as the air-fuel ratio sensor 40, 41. FIG. 2 is used to simply describe the structure of the air-fuel ratio sensor 40, 41. The air-fuel ratio sensor 40, 41 has a solid electrolyte layer 51, an exhaust side electrode 52 provided on a side surface of the solid electrolyte layer 51, an atmosphere side electrode 53 provided on the other side surface of the solid electrolyte layer 51, a diffusion speed controlling layer 54 that controls a diffusion speed of the flowing exhaust gas, a reference gas chamber 55, and a heating portion 56 for heating the air-fuel ratio sensor 40, 41, especially for heating the solid electrolyte layer 51 (element).

Especially in the cup-shaped air-fuel ratio sensor 40, 41 in the present embodiment, the solid electrolyte layer 51 is formed into a cylindrical shape having one closed end. An atmospheric gas (air) is introduced into the reference gas chamber 55 delimited inside the cup-shaped air-fuel ratio sensor 40, 41, and the heating portion 56 is provided. The atmosphere side electrode 53 is provided on an inner surface of the solid electrolyte layer 51, and the exhaust side electrode 52 is provided on an outer surface of the solid electrolyte layer 51. The diffusion speed controlling layer 54 is provided on the outer surfaces of the solid electrolyte layer 51 and the exhaust side electrode 52 so as to cover them. It should be noted that a protection layer (not shown) for preventing a liquid and the like from being attached to a surface of the diffusion speed controlling layer 54 can be provided on an outer side of the diffusion speed controlling layer 54.

The solid electrolyte layer 51 is formed by a sintered body of an oxygen ion conductive oxide that has distributed CaO, MgO, $Y_2O_3$, $Yb_2O_3$ or the like as a stabilizer to $ZrO_2$ (zirconium oxide), $HfO_2$, $ThO_2$, $Bi_2O_3$ or the like. Moreover, the diffusion speed controlling layer 54 is formed by a porous sintered body of a heat resistant inorganic substance such as aluminum oxide, magnesium oxide, silicious stone, spinel and mullite. Moreover, the exhaust side electrode 52 and the atmosphere side electrode 53 are formed by a noble metal having a high catalyst activity, such as platinum.

Moreover, a sensor applied voltage V is applied between the exhaust side electrode 52 and the atmosphere side electrode 53 by an applied voltage control device 60 mounted on the ECU 31. Moreover, a current detection device 61 for detecting a current I flowing between these electrodes 52, 53 via the solid electrolyte layer 51 when applying the sensor applied voltage is provided on the ECU 31. The current detected by the current detection device 61 is an output current of the air-fuel ratio sensor 40, 41.

Figure 3:
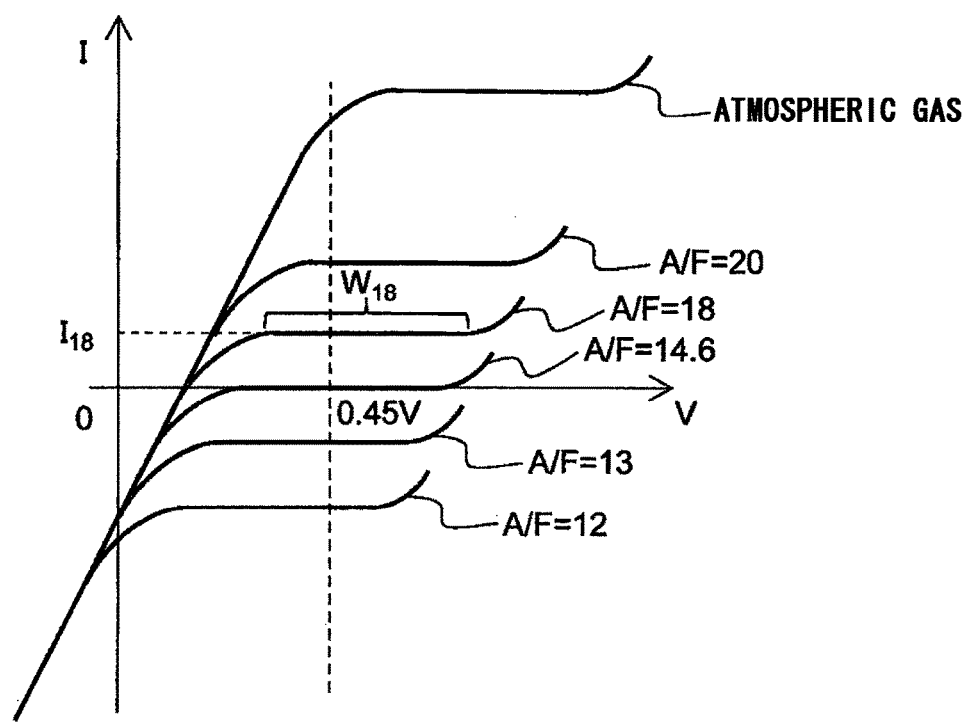
FIG. 3 is a view showing a relationship between a sensor applied voltage and an output current under respective exhaust air-fuel ratios.

The air-fuel ratio sensor 40, 41 formed in this manner has voltage-current (V-I) characteristics as shown in FIG. 3. It can be seen from FIG. 3 that the larger the exhaust air-fuel ratio is (the leaner it becomes), the larger the output current I is. Moreover, in a V-I line under the respective exhaust air-fuel ratios, there exists an area parallel to a V-axis, i.e., an area in which the output current almost does not change even if the sensor applied voltage changes. This voltage area is referred to as a limit current area, and the current at this time is referred to as a limit current. In FIG. 3, the limit current area and the limit current when the exhaust air-fuel ratio is 18 are respectively denoted by $W_{18}$ and $I_{18}$.

On the other hand, in an area in which the sensor applied voltage is lower than the limit current area, the output current changes substantially in proportion to the sensor applied voltage. Such an area is hereinafter referred to as a proportional area. A slope at this time is determined by a direct current element resistance of the solid electrolyte layer 51. Moreover, in an area in which the sensor applied voltage is higher than the limit current area, the output current increases along with the increase of the sensor applied voltage. In this area, since a case of a decomposition of water contained in the exhaust gas and the like are produced on the exhaust side electrode 52, the output voltage changes corresponding to the change of the sensor applied voltage. Such an area is hereinafter referred to as a water decomposition area.

Figure 4:
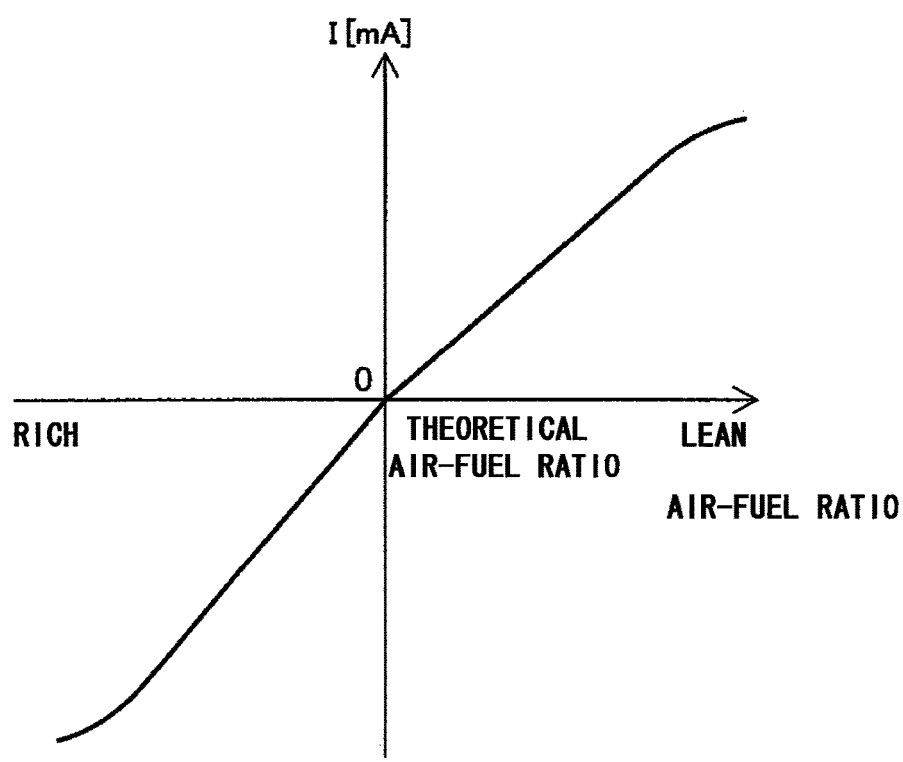
FIG. 4 is a view showing a relationship between the exhaust air-fuel ratio and the output current when the applied voltage is fixed.

FIG. 4 is a view showing a relationship between the exhaust air-fuel ratio and the output current I when the applied voltage is constant at about 0.45V. It can be seen from FIG. 4 that in the air-fuel ratio sensor 40, 41, the larger the exhaust air-fuel ratio is (that is, the leaner it becomes), the larger the output current I from the air-fuel ratio sensor 40, 41 is. Moreover, the air-fuel ratio sensor 40, 41 is configured such that the output current I becomes zero when the exhaust air-fuel ratio is the theoretical air-fuel ratio.

It should be noted that in the above example, an air-fuel ratio sensor of a limit current type having a structure as shown in FIG. 2 is used as the air-fuel ratio sensor 40, 41. However, an air-fuel ratio sensor of a limit current type having another structure such as a laminated air-fuel ratio sensor of a limit current type, or an arbitrary air-fuel ratio sensor such as one that is not an air-fuel ratio sensor of a limit current type can be used as an upstream side air-fuel ratio sensor 40.

<Basic Control>

In the internal combustion engine configured in this manner, a fuel injection amount from the fuel injection valve 11 is set, by making the air-fuel ratio of the exhaust gas flowing into the upstream side exhaust purification catalyst 20 become an optimal air-fuel ratio based on an engine operation state on the basis of outputs of the two air-fuel ratio sensors 40, 41. As such a method of setting the fuel injection amount, the following method can be listed: performing a feedback control by making the air-fuel ratio of the exhaust gas flowing into the upstream side exhaust purification catalyst 20 (or the air-fuel ratio of the exhaust gas flowing out of the engine body) become a target air-fuel ratio on the basis of the output of the upstream side air-fuel ratio sensor 40. Moreover, the output of the upstream side air-fuel ratio sensor 40 is revised or the target air-fuel ratio is modified, on the basis of an output of the downstream side air-fuel ratio sensor 41.

Figure 5:
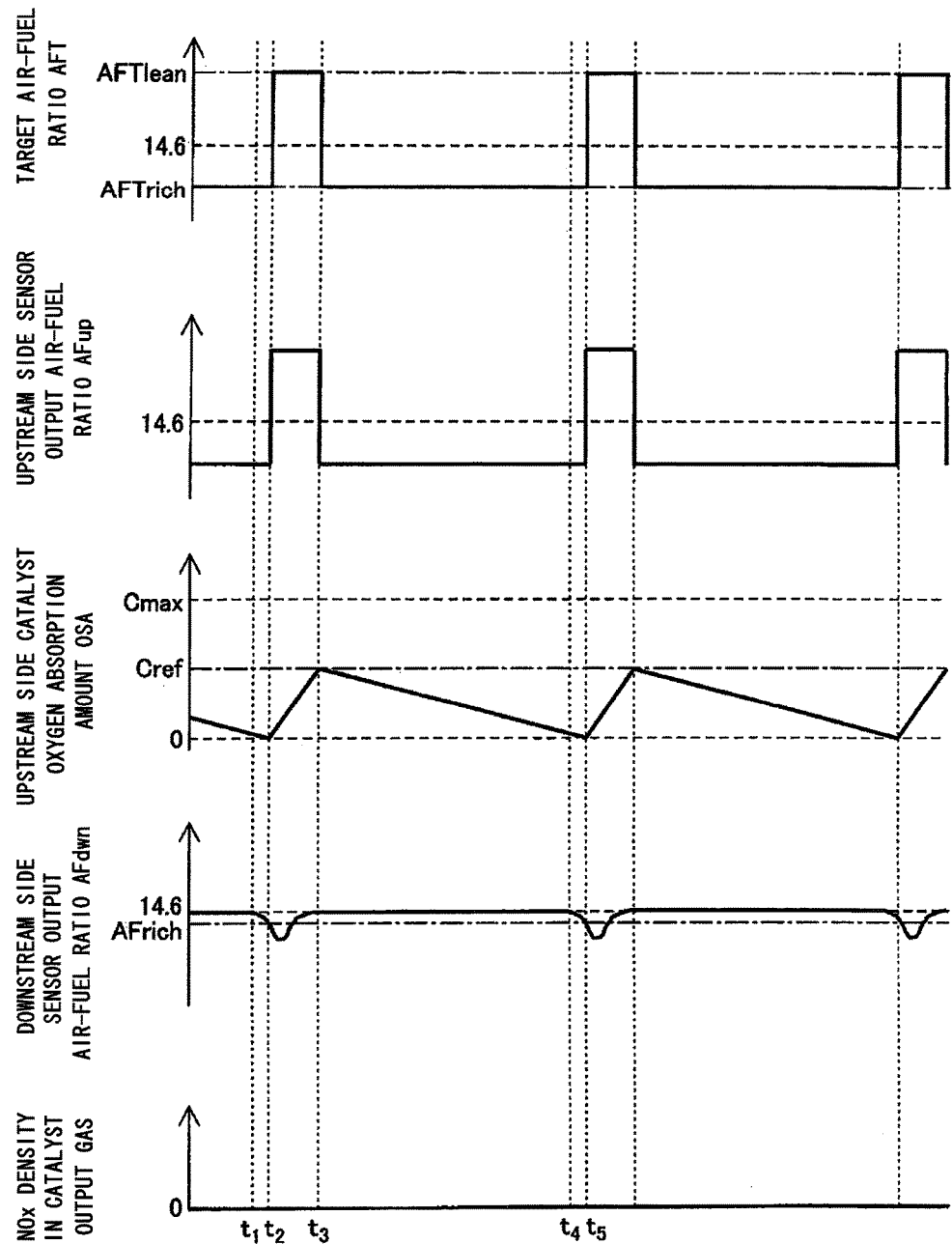
FIG. 5 is a time chart of a target air-fuel ratio and the like when an air-fuel ratio control is performed.

Referring to FIG. 5, an example of a control of such a target air-fuel ratio is simply described.

FIG. 5 is a time chart of a target air-fuel ratio AFT, an output air-fuel ratio AFup of the upstream side air-fuel ratio sensor 40, an oxygen absorption amount OSA of the upstream side exhaust purification catalyst and an output air-fuel ratio AFdwn of the downstream side air-fuel ratio sensor 41 during a normal operation of the internal combustion engine. It should be noted that the "output air-fuel ratio" refers to an air-fuel ratio corresponding to the output of the air-fuel ratio sensor. Moreover, the expression "a normal operation (normal control)" refers to an operation state (control state) that has not undergone a control that adjusts the fuel injection amount in accordance with a specific operation state of the internal combustion engine (for example, an increment correction of the fuel injection amount performed when a vehicle carrying an internal combustion engine accelerates, a fuel cut-off control described later, etc.).

In the example as shown in FIG. 5, when the output air-fuel ratio AFdwn of the downstream side air-fuel ratio sensor 41 is below a rich judgment reference air-fuel ratio (e.g., 14.55), the target air-fuel ratio is set to and maintained as a lean set air-fuel ratio AFTlean (e.g., 15). Then, the oxygen absorption amount of the upstream side exhaust purification catalyst 20 is deduced, and when the deduced value becomes one equal to or larger than a predetermined judgment reference absorption amount Cref (an amount less than a maximum oxygen absorbability amount Cmax), the target air-fuel ratio is set to and maintained as a rich set air-fuel ratio AFTrich (e.g., 14.4). In the example as shown in FIG. 5, such an operation is repeated.

To be specific, in the example as shown in FIG. 5, before a time $t_1$, the target air-fuel ratio AFT is the rich set air-fuel ratio AFTrich, and along with this, the output air-fuel ratio AFup of the upstream side air-fuel ratio sensor 40 also becomes a rich air-fuel ratio. Moreover, since oxygen is absorbed in the upstream side exhaust purification catalyst 20, the output air-fuel ratio AFdwn of the downstream side air-fuel ratio sensor 41 becomes substantially the theoretical air-fuel ratio (14.6). At this time, the air-fuel ratio of the exhaust gas flowing into the upstream side exhaust purification catalyst 20 becomes the rich air-fuel ratio, so the oxygen absorption amount of the upstream side exhaust purification catalyst 20 is gradually reduced.

Then, at the time $t_1$, the oxygen absorption amount of the upstream side exhaust purification catalyst 20 is close to zero, thus part of gases that have not been combusted flowing into the upstream side exhaust purification catalyst 20 begins flowing out without being purified by the upstream side exhaust purification catalyst 20. As a result, at a time $t_2$, the output air-fuel ratio AFdwn of the downstream side air-fuel ratio sensor 41 becomes the rich judgment reference air-fuel ratio AFrich that is slightly richer than the theoretical air-fuel ratio, and at this time, the target air-fuel ratio switches from the rich set air-fuel ratio AFTrich to the lean set air-fuel ratio AFTlean.

By means of switching of the target air-fuel ratio, the air-fuel ratio of the exhaust gas flowing into the upstream side exhaust purification catalyst 20 becomes a lean air-fuel ratio, and the outflow of the gas that has not been combusted is decreased or stopped. Moreover, the oxygen absorption amount OSA of the upstream side exhaust purification catalyst 20 gradually increases, and reaches the judgment reference absorption amount Cref at a time $t_3$. In this way, when the oxygen absorption amount reaches the judgment reference absorption amount Cref, the target air-fuel ratio switches again from the lean set air-fuel ratio AFTlean to the rich set air-fuel ratio AFTrich. By means of the switching of the target air-fuel ratio, the air-fuel ratio of the exhaust gas flowing into the upstream side exhaust purification catalyst 20 becomes again the rich air-fuel ratio. As a result, the oxygen absorption amount of the upstream side exhaust purification catalyst 20 gradually decreases, and such an operation is repeated afterwards. By performing such a control, the outflow of the NOx from the upstream side exhaust purification catalyst 20 can be prevented.

It should be noted that the control of the air-fuel ratio performed during the normal operation is not necessarily limited to a control based on outputs of the upstream side air-fuel ratio sensor 40 and the downstream side air-fuel ratio sensor 41 as described above. The control can be an arbitrary control as long as it is a control based on the outputs of the air-fuel ratio sensors 40, 41. Accordingly, for example, as a control performed during the normal operation, a control that fixes the target air-fuel ratio as the theoretical air-fuel ratio, that performs the feedback control by making the output air-fuel ratio AFup of the upstream side air-fuel ratio sensor 40 become the theoretical air-fuel ratio, and that revises the output air-fuel ratio AFup of the upstream side air-fuel ratio sensor 40 based on the output air-fuel ratio AFup of the downstream side air-fuel ratio sensor 41, can be performed.

Moreover, in the internal combustion engine of the present embodiment, when the vehicle in which the internal combustion engine is mounted decelerates or the like, the fuel cut-off control that makes the fuel injection from the fuel injection valve 11 be stopped or greatly reduced to make the fuel supply to the combustion chamber 5 be stopped or greatly decreased in the operation of the internal combustion engine is executed.

Such a fuel cut-off control begins when a prescribed condition for beginning a fuel cut-off is satisfied. To be specific, the fuel cut-off control is executed, for example, when a operating amount of the accelerator pedal 42 is zero or substantially zero (i.e., an engine load is zero or substantially zero), and the engine speed is equal to or larger than a prescribed speed higher than a speed during idling.

When the fuel cut-off control is performed, air or an exhaust gas similar to the air is discharged from the internal combustion engine, so a gas having an extremely large air-fuel ratio (i.e., having an extremely high lean degree) flows into the upstream side exhaust purification catalyst 20. As a result, during the fuel cut-off control, a large amount of oxygen flows into the upstream side exhaust purification catalyst 20, and the oxygen absorption amount of the upstream side exhaust purification catalyst 20 reaches a maximum oxygen absorbability amount.

Moreover, in the internal combustion engine of the embodiment, in order to discharge the oxygen absorbed in the upstream side exhaust purification catalyst 20 during the fuel cut-off control, after the fuel cut-off control just finishes, an after-restoration richness control that makes the air-fuel ratio of the exhaust gas flowing into the upstream side exhaust purification catalyst 20 become an after-restoration rich air-fuel ratio richer than the rich set air-fuel ratio is performed.

<Abnormality Diagnosis of an Air-Fuel Ratio Sensor>

However, as mentioned above, the air-fuel ratio sensor 40, 41 is deteriorated along with its use, and an abnormality sometimes will be produced in the air-fuel ratio sensor 40, 41. When the abnormality is produced in the air-fuel ratio sensor 40, 41, the accuracy of the output thereof is deteriorated, thereby the fuel injection amount from the fuel injection valve 11 cannot be properly controlled. As a result, deterioration of an exhaust emission or deterioration of utilization of the fuel will be resulted in. Accordingly, most of control devices of the internal combustion engines perform the abnormality diagnosis control that diagnoses by the control devices themselves the abnormality of the air-fuel ratio sensor 40, 41.

As such an abnormality diagnosis control, a control that is performed during the fuel cut-off control, for example, can be listed. To be specific, the abnormality diagnosis is performed on the basis of a transition of the output air-fuel ratio of the air-fuel ratio sensor 40, 41 when the fuel cut-off control begins and when the fuel cut-off control is completed.

Figure 6:
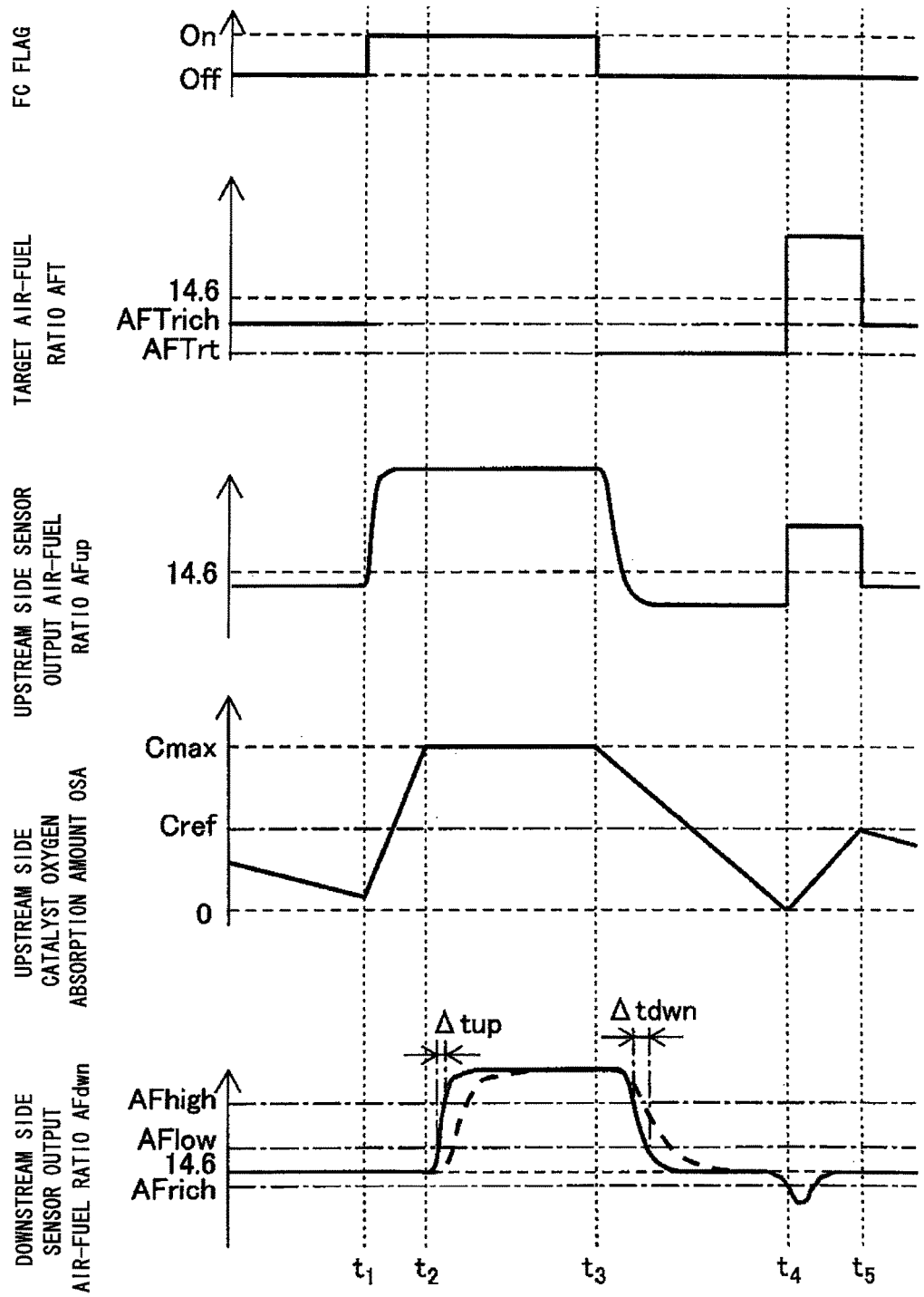
FIG. 6 is a time chart of the target air-fuel ratio and the like when a fuel cut-off control is performed.

FIG. 6 is a time chart of the target air-fuel ratio AFT, the output air-fuel ratio AFup of the upstream side air-fuel ratio sensor 40, the oxygen absorption amount OSA of the upstream side exhaust purification catalyst 20 and the output air-fuel ratio AFdwn of the downstream side air-fuel ratio sensor 41 when a fuel cut-off control is performed. In the example as shown in FIG. 6, the fuel cut-off control is begun (FC flag ON) at a time $t_1$, and the fuel cut-off control is completed (FC flag OFF) at a time $t_3$.

In the example as shown in FIG. 6, at the time $t_1$, the air-fuel ratio control during the normal operation as described above is performed before the fuel cut-off control is begun. At the time $t_1$, when the fuel cut-off control is begun, a gas of a lean air-fuel ratio having a large lean degree is discharged from the engine body 1, thus the output air-fuel ratio AFup of the upstream side air-fuel ratio sensor 40 rises sharply. At this time, the oxygen in the exhaust gas flowing into the upstream side exhaust purification catalyst 20 is absorbed in the upstream side exhaust purification catalyst 20, so the oxygen absorption amount of the upstream side exhaust purification catalyst 20 increases, and on the other hand, the output air-fuel ratio AFdwn of the downstream side air-fuel ratio sensor 41 is still the theoretical air-fuel ratio.

Then, at a time $t_2$, when the oxygen absorption amount of the upstream side exhaust purification catalyst 20 reaches the maximum oxygen absorbability amount (Cmax), the upstream side exhaust purification catalyst 20 cannot further absorb the oxygen. Accordingly, after the time $t_2$, the output air-fuel ratio AFdwn of the downstream side air-fuel ratio sensor 41 also rises sharply.

At the time $t_3$, when a condition for completing the fuel cut-off is satisfied, the fuel cut-off control is completed. As the condition for completing the fuel cut-off, a case that the operating amount of the accelerator pedal 42 becomes one equal to or larger than a prescribed value (i.e., a case that the engine load becomes a value to a certain extent) or a case that the engine speed becomes one below the prescribed speed higher than the speed during idling, for example, can be listed.

When the fuel cut-off control is completed, the after-restoration richness control is performed in order to discharge the oxygen absorbed in the upstream side exhaust purification catalyst 20 during the fuel cut-off control. In the after-restoration richness control, the target air-fuel ratio of the exhaust gas flowing into the upstream side exhaust purification catalyst 20 is set to the after-restoration rich air-fuel ratio AFTrt richer than the rich set air-fuel ratio AFTrich. Along with this, the output air-fuel ratio AFup of the upstream side air-fuel ratio sensor 40 becomes the rich air-fuel ratio, and the oxygen absorption amount OSA of the upstream side exhaust purification catalyst 20 gradually decreases. At this time, even if an exhaust gas having a rich air-fuel ratio is made to flow into the upstream side exhaust purification catalyst 20, since the oxygen absorbed in the upstream side exhaust purification catalyst 20 reacts with the gas that has not be combusted in the exhaust gas, the air-fuel ratio of the exhaust gas discharged from the upstream side exhaust purification catalyst 20 also substantially becomes the theoretical air-fuel ratio. Accordingly, the output air-fuel ratio AFdwn of the downstream side air-fuel ratio sensor 41 becomes substantially the theoretical air-fuel ratio.

When the oxygen absorption amount continuously decreases, the oxygen absorption amount becomes substantially zero at last, and the gas that has not been combusted flows out of the upstream side exhaust purification catalyst 20. Thus, at a time $t_4$, the output air-fuel ratio AFdwn of the downstream side air-fuel ratio sensor 41 becomes one below the rich judgment air-fuel ratio AFrich. In this way, when the output air-fuel ratio AFdwn of the downstream side air-fuel ratio sensor 41 reaches one below the rich judgment air-fuel ratio AFrich, the after-restoration richness control is completed. Then, the air-fuel ratio control during the normal operation is begun, and in the example as shown in FIG. 6, the control is performed by alternately setting the air-fuel ratio of the exhaust gas flowing into the upstream side exhaust purification catalyst 20 to the rich air-fuel ratio and the lean air-fuel ratio.

In the case where no abnormality occurs in the downstream side air-fuel ratio sensor 41, when the fuel cut-off control is performed in this manner, as shown by the solid line in FIG. 6, the output air-fuel ratio AFdwn of the downstream side air-fuel ratio sensor 41 sharply changes from the theoretical air-fuel ratio to the lean air-fuel ratio along with beginning of the fuel cut-off control. Moreover, along with completion of the fuel cut-off control, the output air-fuel ratio AFdwn of the downstream side air-fuel ratio sensor 41 sharply changes from the lean air-fuel ratio to the theoretical air-fuel ratio.

On the other hand, in the case where an abnormality occurs in the downstream side air-fuel ratio sensor 41, especially in the case where an abnormality of a reduced response speed occurs, as shown by the broken line in FIG. 6, when the fuel cut-off control is begun, a speed at which the output air-fuel ratio AFdwn of the downstream side air-fuel ratio sensor 41 rises is not fast. Similarly, when the fuel cut-off control is completed, a speed at which the output air-fuel ratio AFdwn of the downstream side air-fuel ratio sensor 41 drops is not fast. That is, in the case where an abnormality of a reduced response speed occurs in the downstream side air-fuel ratio sensor 41, as compared with the case that no abnormality occurs, the speeds at which the output air-fuel ratio AFdwn of the downstream side air-fuel ratio sensor 41 rises and drops when the fuel cut-off control begins and finishes become slow.

Accordingly, in the present embodiment, after the beginning of the fuel cut-off control, a time (hereinafter referred to as a "rising time") Δtup taken by the output air-fuel ratio AFdwn of the downstream side air-fuel ratio sensor 41 to reach a high reference air-fuel ratio AFhigh (e.g., 18) from a low reference air-fuel ratio AFlow (e.g. 15.5) is detected. In the case where the rising time Δtup detected in this manner is shorter than a predetermined reference rising time, it is judged that no abnormality occurs in the downstream side air-fuel ratio sensor 41. On the other hand, in the case where the rising time Δtup detected in this manner is equal to or larger than the predetermined reference rising time, it is judged that an abnormality occurs in the downstream side air-fuel ratio sensor 41.

Similarly, in the present embodiment, after the completion of the fuel cut-off control, a time (hereinafter referred to as a "dropping time") Δtdwn taken by the output air-fuel ratio AFdwn of the downstream side air-fuel ratio sensor 41 to reach the low reference air-fuel ratio AFlow from the high reference air-fuel ratio AFhigh is detected. In the case where the dropping time Δtdwn detected in this manner is shorter than the predetermined reference dropping time, it is judged that no abnormality occurs in the downstream side air-fuel ratio sensor 41. On the other hand, in the case where the dropping time Δtdwn detected in this manner is equal to or larger than the predetermined reference dropping time, it is judged that an abnormality occurs in the downstream side air-fuel ratio sensor 41.

A result of performing the abnormality diagnosis in this manner is, for example, to lighten a warning lamp that notifies a user of the abnormality of the downstream side air-fuel ratio sensor 41 in the case where it is judged that an abnormality occurs in the downstream side air-fuel ratio sensor 41.

It should be noted that in the above example, only the abnormality diagnosis of the downstream side air-fuel ratio sensor 41 is described, but the abnormality diagnosis of the upstream side air-fuel ratio sensor 40 can be also performed. Moreover, the abnormality diagnosis of the air-fuel ratio sensor 40, 41 can be a diagnosis of other abnormalities than the abnormality of the reduced response speed. Especially in the abnormality diagnosis control of the air-fuel ratio sensor 40, 41, as long as being performed during or before or after the fuel cut-off control, a control by another method can be performed in addition to the abnormality diagnosis control or a control by another method can be separately performed in a different manner. As one of such controls, a control that detects the output air-fuel ratio of the downstream side air-fuel ratio sensor 41 that is finally converged during the fuel cut-off control, for example, can be listed. In this case, the low reference air-fuel ratio or the high reference air-fuel ratio is revised based on the converged output air-fuel ratio during the fuel cut-off control.

<Problems of an Abnormality Diagnosis>

Figure 7:
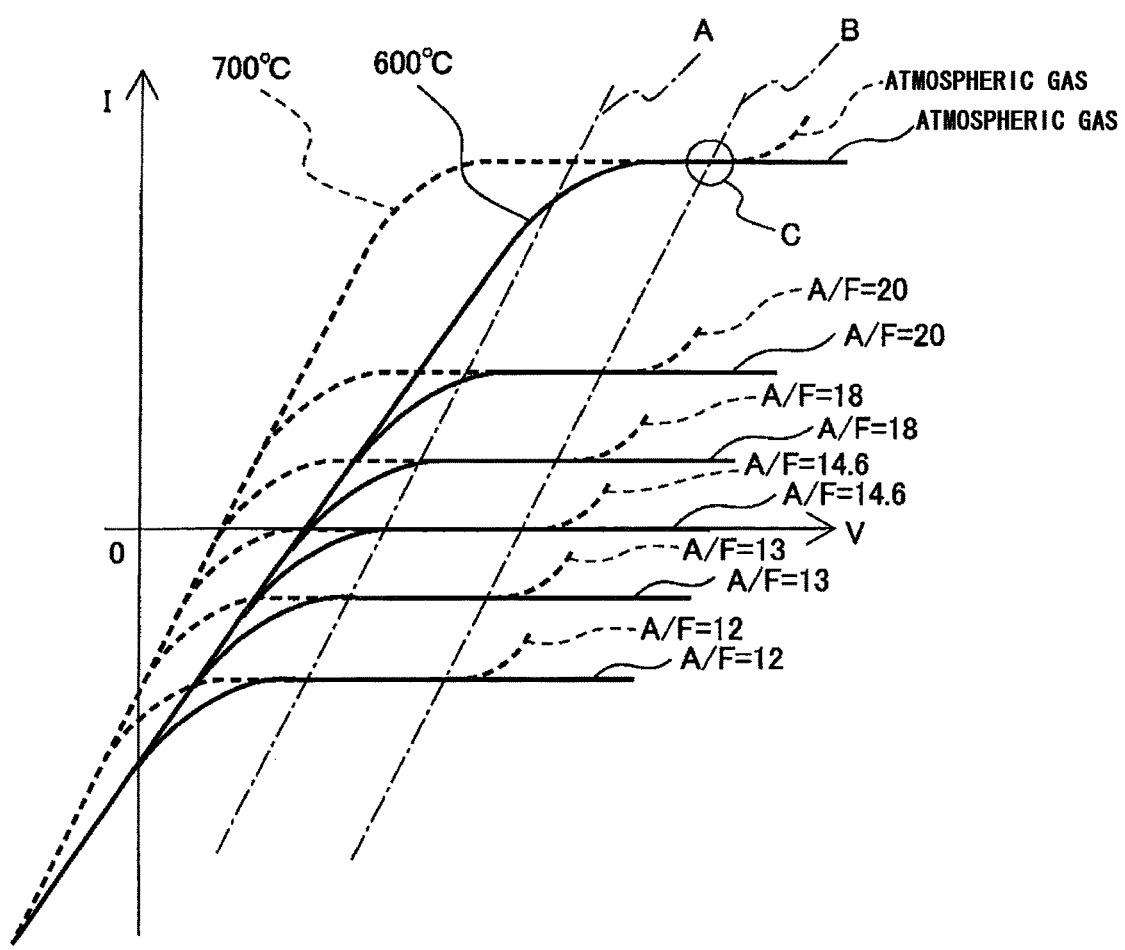
FIG. 7 is a view showing a relationship between the sensor applied voltage and the output current under the respective exhaust air-fuel ratios.

However, the voltage-current (V-I) characteristics of the air-fuel ratio sensor 40, 41 change in accordance with a temperature. This case is as shown in FIG. 7. The solid line in FIG. 7 denotes the voltage-current characteristics when an element temperature of the air-fuel ratio sensor 40, 41 is 600° C., and the broken line in FIG. 7 denotes the voltage-current characteristics when the element temperature of the air-fuel ratio sensor 40, 41 is 700° C.

It can be seen from FIG. 7 that with respect to the slope of the proportional area, the slope when the element temperature is 700° C. is larger than the slope when the element temperature is 600° C. As a result, for example, in the case where a feedback control is performed with respect to the sensor applied voltage of the air-fuel ratio sensor 40, 41 like A in FIG. 7 in accordance with the current I, when the element temperature is 700° C., even the air-fuel ratio of the atmospheric gas can be detected by the air-fuel ratio sensor 40, 41. However, in the case where the feedback control is performed with respect to the sensor applied voltage like A, when the element temperature is 600° C., the air-fuel ratio of the atmospheric gas or a lean air-fuel ratio having a comparatively high lean degree has not been detected in the limit current area. As a result, the air-fuel ratio of the atmospheric gas or the exhaust gas of the lean air-fuel ratio having a comparatively high lean degree cannot be accurately detected by the air-fuel ratio sensor 40, 41.

On the other hand, when the feedback control is performed with respect to the sensor applied voltage of the air-fuel ratio sensor 40, 41 like B in FIG. 7 in accordance with the current I, in an area where the atmospheric gas is detected (C in FIG. 7), the sensor applied voltage rises. Accordingly, so-called blackening is produced in the solid electrolyte layer 51. Accordingly, the case that the feedback control is performed with respect to the sensor applied voltage like B in FIG. 7 is not practical.

Thus, in order to accurately monitor the air-fuel ratio of the atmospheric gas or the exhaust gas of the lean air-fuel ratio having a comparatively high lean degree, it is required that the element temperature of the air-fuel ratio sensor 40, 41 should be one equal to or larger than 700° C. However, in order to maintain all the time the element temperature of the air-fuel ratio sensor 40, 41 as one equal to or larger than 700° C., the electric power consumed by the heating of the solid electrolyte layer 51 by the heating portion 56 becomes large.

On the other hand, it is also considered to make the element temperature of the air-fuel ratio sensor 40 be about 600° C. normally, and to raise the element temperature to about 700° C. by the heating portion 56 only when performing the abnormality diagnosis of the air-fuel ratio sensor 40, 41. However, a time to an extent will be taken to make the element temperature of the air-fuel ratio sensor 40, 41 rise from about 600° C. to about 700° C. Accordingly, even if heating of the air-fuel ratio sensor 40, 41 is performed along with beginning of the fuel cut-off control, the fuel cut-off control is almost completed before the element temperature reaches 700° C. As a result, the above-mentioned abnormality diagnosis cannot be performed in a state where the temperature of the air-fuel ratio sensor 40, 41 is high, thus the abnormality diagnosis of the air-fuel ratio sensor 40, 41 cannot be accurately performed.

<Temperature Control of the Invention>

Accordingly, in the embodiment, a feedback control is performed with respect to a heating amount of the heating portion 56 of the air-fuel ratio sensor 40, 41 by making the element temperature of the air-fuel ratio sensor 40, 41 become the target element temperature. Moreover, in the embodiment, the target element temperature during a temperature rise period from a time when a prescribed temperature rise begins after a start of the engine to a time when the prescribed temperature rise is completed after a completion of the abnormality diagnosis control of the air-fuel ratio sensor 40, 41 is set to be higher than the target element temperature outside the temperature rise period.

Figure 8:
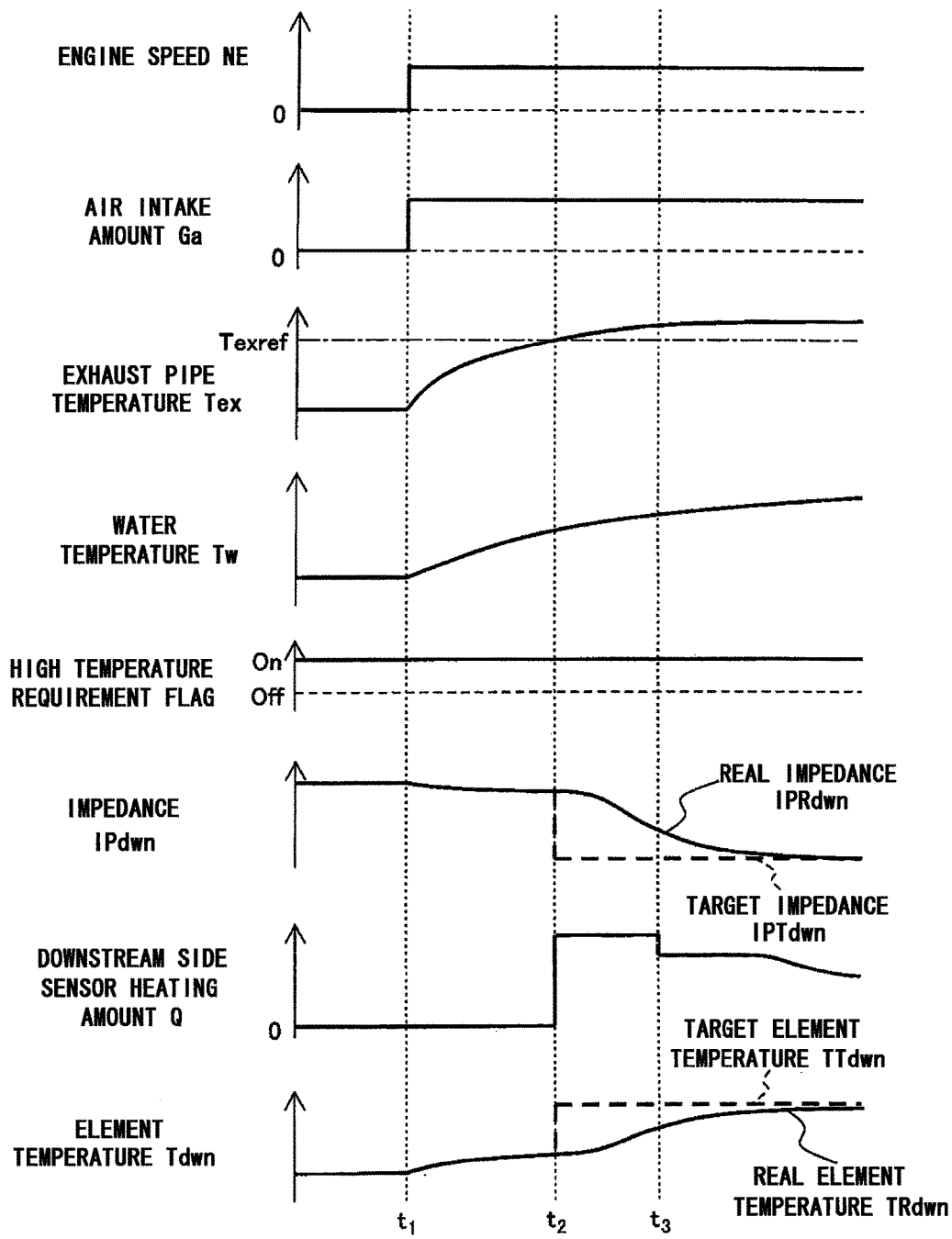
FIG. 8 is a time chart of an engine speed and the like when the internal combustion engine is started.

FIG. 8 is a time chart of an engine speed NE, an air intake amount Ga, a temperature Tex of an exhaust pipe around the downstream side air-fuel ratio sensor 41, a temperature Tw of engine cooling water, a high temperature requirement flag, an impedance IPdwn of the downstream side air-fuel ratio sensor 41, a heating amount Q of the downstream side air-fuel ratio sensor 41 per unit time, and an element temperature Tdwn of the downstream side air-fuel ratio sensor 41 when the internal combustion engine is started. The high temperature requirement flag is set to ON when it is required that the element temperature of the downstream side air-fuel ratio sensor 41 should be higher than a normal one, and is set to OFF in other cases.

It should be noted that the impedance IPdwn of the downstream side air-fuel ratio sensor 41 (more accurately, the impedance of the solid electrolyte layer 51 (element)) of the downstream side air-fuel ratio sensor 41) changes in accordance with the temperature of the solid electrolyte layer 51. To be specific, the higher the temperature of the solid electrolyte layer 51 is, the lower the impedance of the solid electrolyte layer 51 is. Accordingly, in the embodiment, in order to make the element temperature of the downstream side air-fuel ratio sensor 41 become the target element temperature, the feedback control is performed by making a real impedance IPRdwn of the downstream side air-fuel ratio sensor 41 become a target impedance IPTdwn corresponding to the target element temperature.

Moreover, in the embodiment, the impedance of the solid electrolyte layer 51 (element) is detected in order to detect the temperature of the downstream side air-fuel ratio sensor 41. The detection of the impedance of the solid electrolyte layer 51 is performed by applying an alternating voltage of a prescribed frequency to the solid electrolyte layer 51 and on the basis of a magnitude of an alternating current flowing into the solid electrolyte layer 51 along therewith. The application of the alternating voltage can be performed using the electrodes 52, 53, or performed by other methods.

In the example as shown in FIG. 8, at a time $t_1$, an ignition switch is set to ON. Accordingly, at the time $t_1$, the engine speed NE rises, and the air intake amount Ga of the exhaust gas supplied into the combustion chamber 5 increases. Moreover, after the time $t_1$, the exhaust gas discharged from the combustion chamber 5 passes through the exhaust passage, so the temperature Tex of the exhaust pipe 22 around the downstream side air-fuel ratio sensor 41 gradually rises. Moreover, after the time $t_1$, combustion is produced in the combustion chamber 5, so the temperature Tw of the engine cooling water gradually rises.

However, at the time $t_1$, even if the ignition switch is ON and the internal combustion engine is started, no target impedance IPTdwn is set. As a result, the heating amount of the downstream side air-fuel ratio sensor 41 produced by the heating portion 56 is still maintained as zero. Moreover, the element temperature of the downstream side air-fuel ratio sensor 41 slightly rises due to the passage of the exhaust gas, but since no heating based on the heating portion 56 is performed, no obvious change occurs.

Then, the temperature Tex of the exhaust pipe 22 around the downstream side air-fuel ratio sensor 41 gradually rises due to the exhaust gas discharged from the engine body 1, and rises to a reference pipe temperature Texref at a time $t_2$. The reference pipe temperature Texref is equal to or larger than a dew point of water, and preferably equal to or larger than a boiling point. At the time $t_2$, when the temperature Tex of the exhaust pipe 22 reaches the reference pipe temperature Texref, the target impedance IPTdwn of the downstream side air-fuel ratio sensor 41 is set to a low value, thus the heating of the element of the downstream side air-fuel ratio sensor 41 begins. The target element temperature of the downstream side air-fuel ratio sensor 41 at this time is set to a comparatively high temperature (hereinafter referred to as a "high set temperature", e.g., 700° C.), and the target impedance IPTdwn is set to a high temperature corresponding impedance (a comparatively low impedance) corresponding to the high set temperature. That is, in the embodiment, setting the target element temperature to the high set temperature begins when the heating of the element of the downstream side air-fuel ratio sensor 41 is begun. It should be noted that setting the target element temperature to the high set temperature can also begin after the heating of the element of the downstream side air-fuel ratio sensor 41 is begun.

Moreover, in the example as shown in FIG. 8, at a time $t_3$, although the target impedance IPTdwn is maintained constant, the heating amount of the heating portion 56 of the downstream side air-fuel ratio sensor 41 is also reduced. The heating amount is reduced in this manner to prevent the heating portion 56 from excessively rising in temperature. That is, the heating portion 56 generally becomes a high temperature as compared with the solid electrolyte layer 51, so when the heating is performed with the intact heating amount, the temperature of the heating portion 56 itself will become a high temperature above a limit temperature. Accordingly, in the embodiment, the heating amount of the heating portion 56 of the downstream side air-fuel ratio sensor 41 is reduced at the time $t_3$, thereby preventing the case that the heating portion 56 excessively rises in temperature to a temperature above the limit temperature.

In this way, in the embodiment, after the internal combustion engine is started and when the temperature Tex of the exhaust pipe 22 around the downstream side air-fuel ratio sensor 41 becomes one equal to or larger than the reference pipe temperature Texref, the heating by the heating portion 56 begins. Moreover, the target element temperature TTdwn at this time is set to the high set temperature higher than the normal one.

It should be noted that in the embodiment, it is not necessary to detect the temperature Tex of the exhaust pipe 22, and the temperature Tex of the exhaust pipe 22 can be also deduced based on other parameters. Accordingly, the heating can be begun, for example, when an elapsed time after the start of the internal combustion engine or the air intake amount Ga after the start of the internal combustion engine is equal to or larger than a prescribed value.

Figure 9:
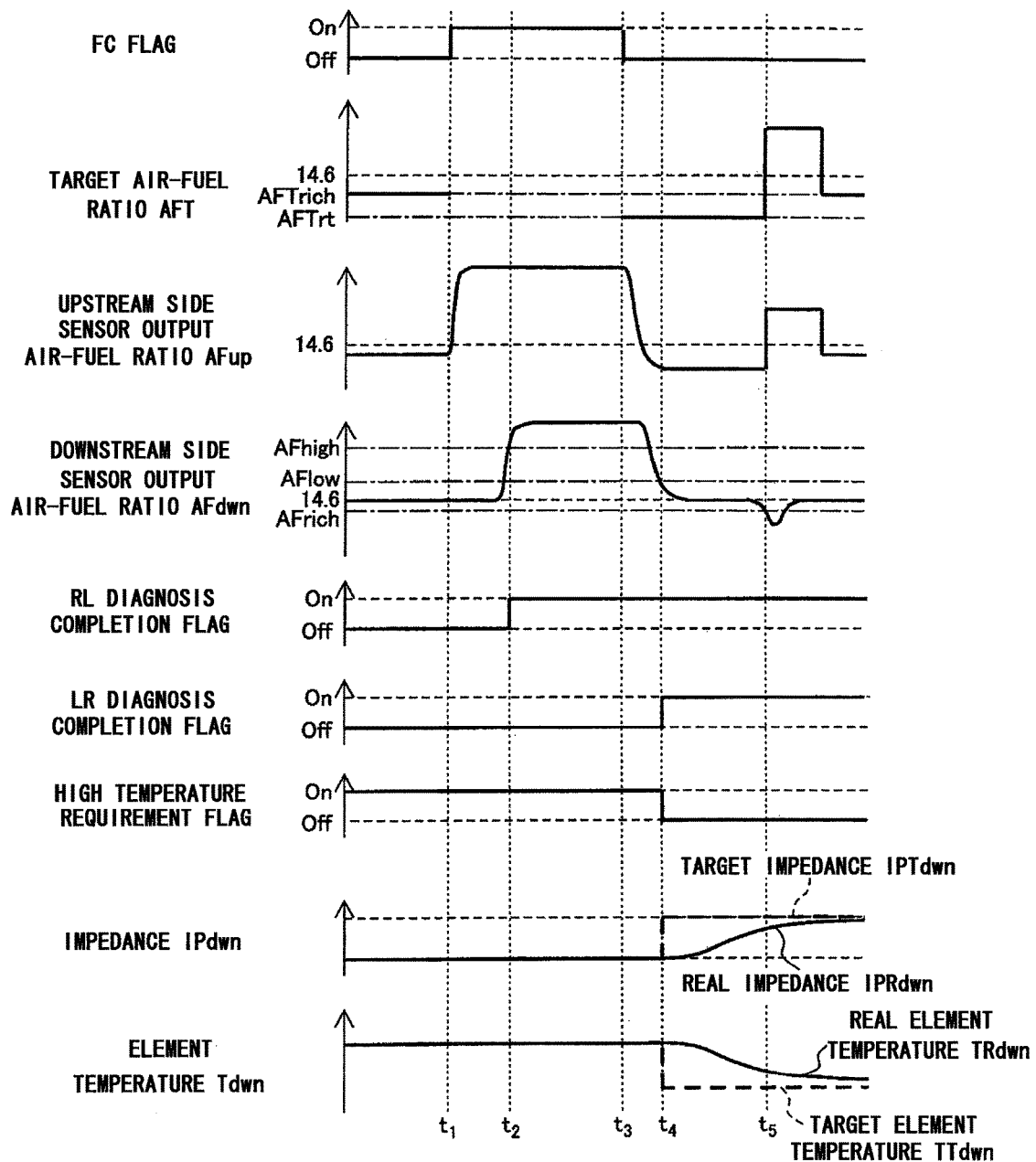
FIG. 9 is a time chart of the target air-fuel ratio and the like when the fuel cut-off control is performed.

FIG. 9 is a time chart of a target air-fuel ratio of an initial fuel cut-off control, an output air-fuel ratio AFup of the upstream side air-fuel ratio sensor 40, an output air-fuel ratio AFdwn of the downstream side air-fuel ratio sensor 41, an RL diagnosis completion flag, an LR diagnosis completion flag, a high temperature requirement flag, an impedance IPdwn of the downstream side air-fuel ratio sensor 41, and an element temperature Tdwn of the downstream side air-fuel ratio sensor 41 after the start of the engine. The RL diagnosis completion flag is a flag denoting whether or not the abnormality diagnosis of the downstream side air-fuel ratio sensor 41 is completed when the output air-fuel ratio AFdwn of the downstream side air-fuel ratio sensor 41 changes from the rich air-fuel ratio or the theoretical air-fuel ratio to the lean air-fuel ratio, i.e., after the fuel cut-off control just begins. Similarly, the LR diagnosis completion flag is a flag denoting whether or not the abnormality diagnosis of the downstream side air-fuel ratio sensor 41 is completed when the output air-fuel ratio AFdwn of the downstream side air-fuel ratio sensor 41 changes from the lean air-fuel ratio to the theoretical air-fuel ratio or the rich air-fuel ratio, i.e., after the fuel cut-off control just finishes.

In the example as shown in FIG. 9, at a time $t_1$, when the condition for beginning the fuel cut-off control as described above is established, the fuel cut-off control is begun. When the fuel cut-off control begins, the output air-fuel ratio AFup of the upstream side air-fuel ratio sensor 40 rises sharply and then slightly slows, and the output air-fuel ratio AFdwn of the downstream side air-fuel ratio sensor 41 also rises. When the output air-fuel ratio AFdwn of the downstream side air-fuel ratio sensor 41 rises along with the beginning of the fuel cut-off control, the rising time Δtup is detected as shown in FIG. 6, and the abnormality diagnosis of the downstream side air-fuel ratio sensor 41 is performed based on the rising time Δtup. Especially at a time $t_2$, when the output air-fuel ratio AFdwn of the downstream side air-fuel ratio sensor 41 reaches the high reference air-fuel ratio AFhigh, the rising time Δtup is calculated, and the abnormality diagnosis of the downstream side air-fuel ratio sensor 41 during the rise of the output air-fuel ratio AFdwn is completed. Accordingly, at the time $t_2$, the RL diagnosis completion flag is set to ON.

In the example as shown in FIG. 9, then, at a time $t_3$, the condition for completing the fuel cut-off control is established, and the fuel cut-off control is completed. When the fuel cut-off control is completed, the output air-fuel ratio AFup of the upstream side air-fuel ratio sensor 40 drops sharply and then slightly slows, and the output air-fuel ratio AFdwn of the downstream side air-fuel ratio sensor 41 also drops. When the output air-fuel ratio AFdwn of the downstream side air-fuel ratio sensor 41 drops along with the completion of the fuel cut-off control, the dropping time Δtdwn is detected as shown in FIG. 6, and the abnormality diagnosis of the downstream side air-fuel ratio sensor 41 is performed based on the dropping time Δtdwn. Especially at a time $t_4$, when the output air-fuel ratio AFdwn of the downstream side air-fuel ratio sensor 41 reaches the low reference air-fuel ratio AFlow, the dropping time Δtdwn is calculated, and the abnormality diagnosis of the downstream side air-fuel ratio sensor 41 during the drop of the output air-fuel ratio AFdwn is completed. Accordingly, at the time $t_4$, the LR diagnosis completion flag is set to ON.

Accordingly, in the example as shown in FIG. 9, at the time $t_4$, the abnormality diagnosis of the downstream side air-fuel ratio sensor 41 performed during the fuel cut-off control is wholly completed. Accordingly, in the embodiment, at the time $t_4$, the target impedance IPTdwn of the downstream side air-fuel ratio sensor 41 rises from the high temperature corresponding impedance to a normal temperature corresponding impedance (an impedance not very low). That is, the target element temperature TTdwn of the downstream side air-fuel ratio sensor 41 drops from the high set temperature (e.g., 700° C.) to a temperature not very high (hereinafter referred to as a "normal set temperature", e.g., 600° C.). Along with this, after the time $t_4$, the real impedance IPRdwn of the downstream side air-fuel ratio sensor 41 gradually rises, and is converged at the normal temperature corresponding impedance after a short while. Accordingly, after the time $t_4$, the real element temperature of the downstream side air-fuel ratio sensor 41 gradually drops, and is converged at a comparatively low temperature after a short while.

In this way, in the embodiment, till the abnormality diagnosis control of the downstream side air-fuel ratio sensor 41 performed during the fuel cut-off control is completed, the target element temperature is set to the high set temperature, and when the abnormality diagnosis is completed, the target element temperature drops to the normal set temperature. Thus, a time when the element temperature of the downstream side air-fuel ratio sensor 41 is raised can be limited to a short time till the completion of the abnormality diagnosis control, thereby the consumed electric power can be suppressed to a comparatively small amount. Moreover, before the beginning of the fuel cut-off control, the element temperature of the downstream side air-fuel ratio sensor 41 is set to a comparatively high one. Accordingly, a case that the temperature of the downstream side air-fuel ratio sensor 41 does not sufficiently rise when the abnormality diagnosis control of the downstream side air-fuel ratio sensor 41 is performed is suppressed.

It should be noted that in the embodiment, the high set temperature is not necessarily about 700° C., and is allowed as long as it is a temperature at which the air-fuel ratio sensor can output a limit current when the atmospheric gas circulates around the air-fuel ratio sensor. That is, in the case where the voltage is applied as shown by A in FIG. 7, a temperature is allowed as long as it is a temperature at which the straight line A and a voltage-current curve at an atmospheric pressure intersects in the limit current area. On the other hand, in the embodiment, the normal set temperature is not necessarily about 600° C., and is allowed as long as it is a temperature at which the detection of the air-fuel ratio can be performed in the limit current area in a normally obtained range of the air-fuel ratio (e.g., 13-17) during the normal operation of the internal combustion engine.

<Flow Chart>

Figure 10:
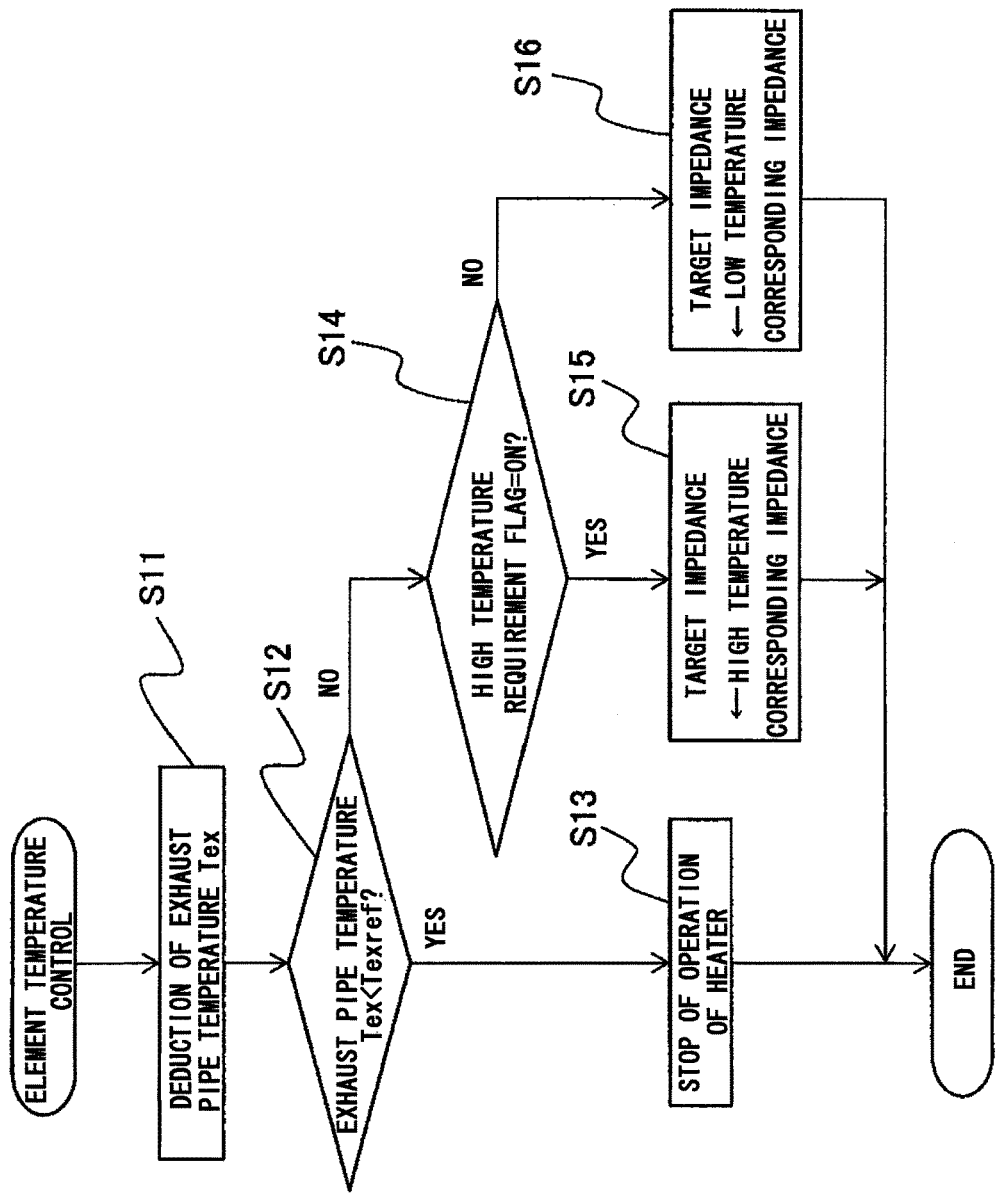
FIG. 10 is a flow chart showing a control routine of an element temperature control of a downstream side air-fuel ratio sensor.

FIG. 10 is a flow chart showing a control routine of an element temperature control of a downstream side air-fuel ratio sensor 41. The control routine as shown in FIG. 10 is carried out at an interval of time.

Firstly, in a step S11, the temperature Tex of the exhaust pipe 22 around the downstream side air-fuel ratio sensor 41 is deduced. The temperature Tex of the exhaust pipe 22 around the downstream side air-fuel ratio sensor 41 is deduced, for example, on the basis of a cooling water temperature Tw before the start of the engine, an elapsed time after the start of the engine and the like. Next, in a step S12, it is judged whether or not the temperature Tex of the exhaust pipe 22 is lower than the reference pipe temperature Texref. In the step S12, in the case where it is judged that the temperature Tex of the exhaust pipe 22 is lower than the reference pipe temperature Texref, a step S13 is entered. In the step S13, the operation of the heating portion 56 is maintained in a stopped state. Accordingly, the heating of the downstream side air-fuel ratio sensor 41 by the heating portion 56 is not performed.

Then, when the temperature Tex of the exhaust pipe 22 gradually rises to reach one equal to or larger than the reference pipe temperature Texref, a step S14 is entered. In the step S14, it is judged whether or not the high temperature requirement flag set in a flag setting control described later is ON. In the case where the high temperature requirement flag is ON, a step S15 is entered, and the target impedance IPTdwn is set to the high temperature corresponding impedance. Thus, the target element temperature TTdwn of the downstream side air-fuel ratio sensor 41 is set to the high set temperature. On the other hand, in the step S14, in the case where it is judged that the high temperature requirement flag is OFF, a step S16 is entered. In the step S16, the target impedance IPTdwn is set to the normal temperature corresponding impedance. Thus, the target element temperature TTdwn of the downstream side air-fuel ratio sensor 41 is set to the normal set temperature.

Figure 11:
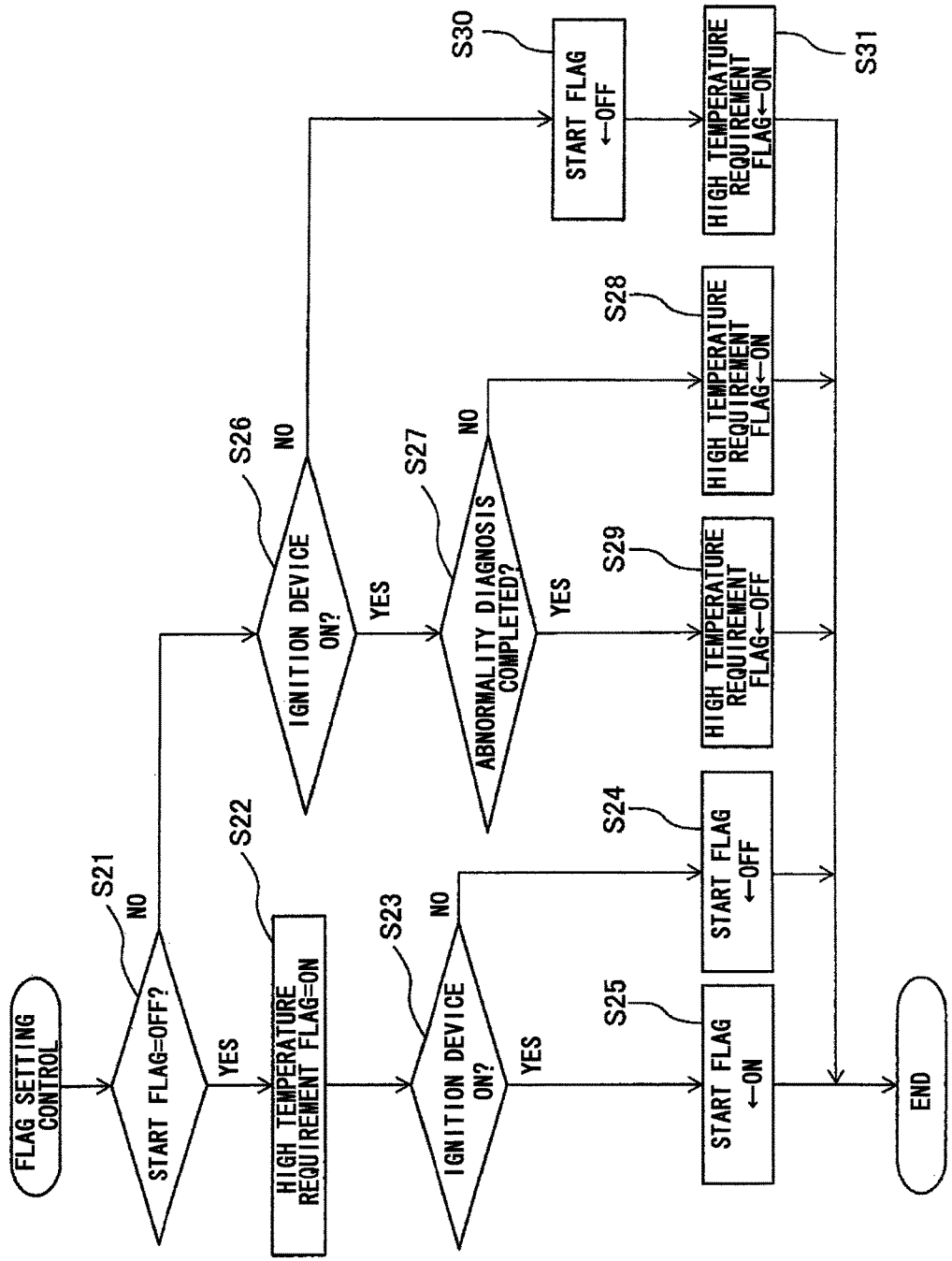
FIG. 11 is a flow chart showing a control routine of a setting control of a high temperature requirement flag.

FIG. 11 is a flow chart showing a control routine of a setting control of a high temperature requirement flag. The control routine as shown in FIG. 11 is performed at an interval of time.

As shown in FIG. 11, firstly in a step S21, it is judged whether or not a start flag is OFF. The start flag is a flag that is set to ON during a period where the ignition switch is ON, and is set to OFF in other cases. In the case where the ignition switch is OFF and the internal combustion engine has not been started, a step S22 is entered. In the step S22, the high temperature requirement flag is set to ON. Next, in a step S23, it is judged whether or not the ignition switch becomes ON. In the case where the ignition switch is OFF, a step S24 is entered, and the start flag is still maintained as OFF. On the other hand, a step S25 is entered in the case where it is judged in the step S23 that the ignition switch becomes ON. In the step S25, the start flag is set to ON, and the control routine is completed.

When the start flag is set to ON, in the following control routine, a step S26 is entered from the step S21. In the step S26, it is judged whether or not the ignition switch is still maintained as ON. In the case where it is judged that the ignition switch is still maintained as ON, a step S27 is entered. In the step S27, it is judged whether or not the abnormality diagnosis of the downstream side air-fuel ratio sensor 41 is completed. Especially in the step S27, it is judged whether or not the abnormality diagnosis performed along with the fuel cut-off control is completed. In the case where it is judged in the step S27 that the abnormality diagnosis of the downstream side air-fuel ratio sensor 41 has not been completed, a step S28 is entered. In the step S28, the high temperature requirement flag is set to ON, and the control routine is completed. As a result, in the temperature control as shown in FIG. 10, the target impedance IPTdwn is set to the high temperature corresponding impedance, and the target element temperature TTdwn of the downstream side air-fuel ratio sensor 41 is set to the high set temperature.

On the other hand, in the step S27, in the case where it is judged that the abnormality diagnosis of the downstream side air-fuel ratio sensor 41 is completed, a step S29 is entered. In the step S29, the high temperature requirement flag is set to OFF, and the control routine is completed. As a result, in the temperature control as shown in FIG. 10, the target impedance IPTdwn is set to the normal temperature corresponding impedance, and the target element temperature TTdwn of the downstream side air-fuel ratio sensor 41 is set to the normal set temperature.

Then, when the ignition switch is OFF, in the following control routine, a step S30 is entered from the step S26. In the step S30, the start flag is set to OFF. Next, in a step S31, the high temperature requirement flag is set to ON, and the control routine is completed.

Second Embodiment

Next, the second embodiment of the invention is described with reference to to FIG. 12 to FIG. 14. The structure and control of the control device of the internal combustion engine of the second embodiment are substantially the same as the structure and control of the control device of the internal combustion engine of the first embodiment. However, in the control device of the second embodiment, the time when the temperature rise begins and the time when the temperature rise is completed during the temperature rise period are different from the periods of the control device of the first embodiment.

Figure 12:
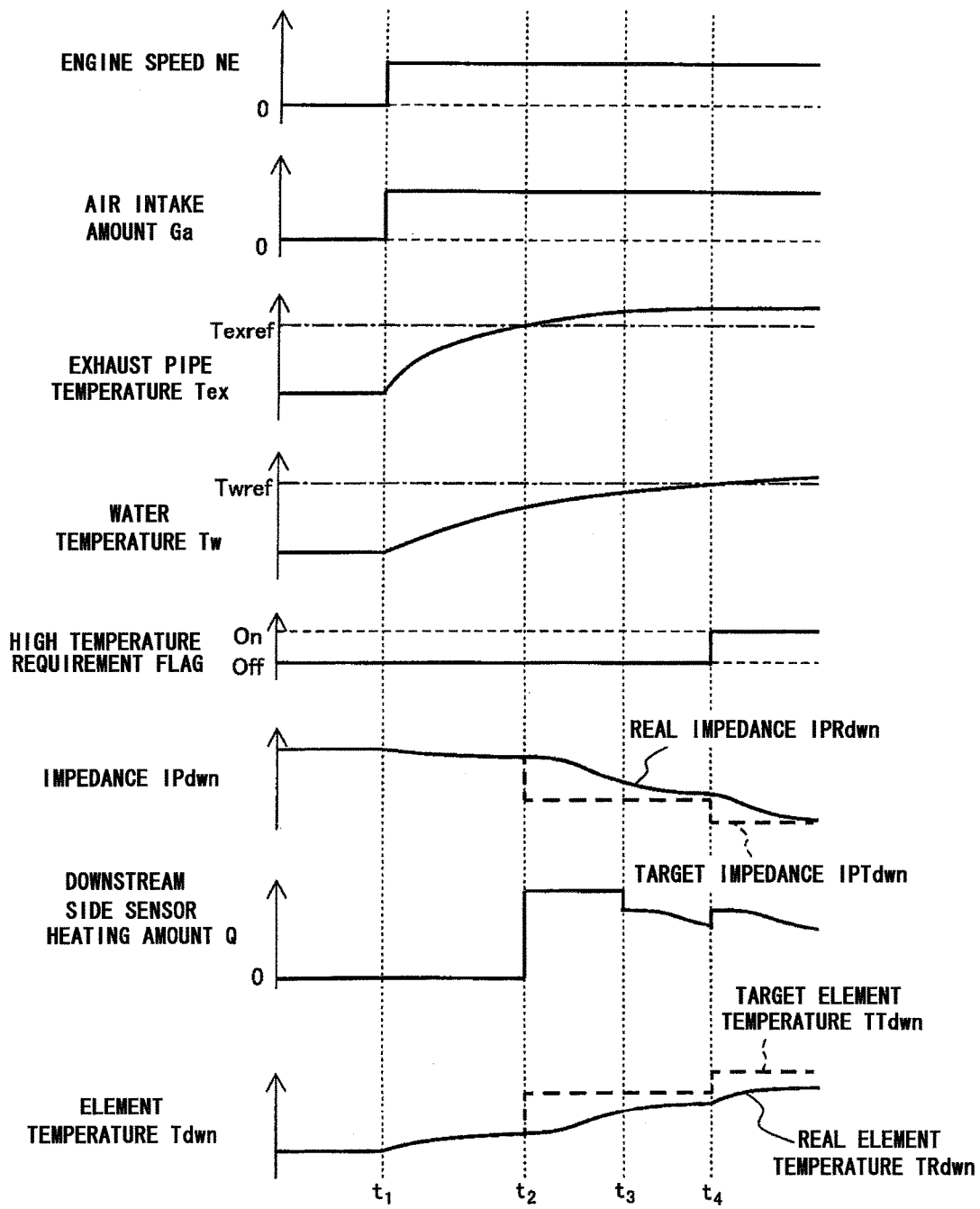
FIG. 12 is a time chart showing the engine speed and the like when the internal combustion engine is started, which is similar to FIG. 8.

FIG. 12 is a time chart showing the engine speed and the like when the internal combustion engine is started, which is similar to FIG. 8. In the example as shown in FIG. 12, at a time $t_1$, the ignition switch is set to ON. Accordingly, after the time $t_1$, the temperature Tex of the exhaust pipe 22 around the downstream side air-fuel ratio sensor 41 gradually rises, and the temperature Tw of the engine cooling water also gradually rises. Moreover, in the example as shown in FIG. 12, till the temperature Tex of the exhaust pipe 22 rises to the reference pipe temperature Texref at a time $t_2$, the target impedance IPTdwn has not been set. As a result, the heating amount of the heating portion 56 with respect to the downstream side air-fuel ratio sensor 41 is still maintained as zero.

Then, the temperature Tex of the exhaust pipe 22 around the downstream side air-fuel ratio sensor 41 gradually rises due to the exhaust gas discharged from the engine body 1, and rises to the reference pipe temperature Texref at a time $t_2$. At the time $t_2$, when the temperature Tex of the exhaust pipe 22 reaches the reference pipe temperature Texref, the target impedance IPTdwn of the downstream side air-fuel ratio sensor 41 is set to the normal temperature corresponding impedance, thus the heating of the downstream side air-fuel ratio sensor 41 begins. Accordingly, the target element temperature TTdwn of the downstream side air-fuel ratio sensor 41 at this time is set to the normal set temperature. When the target impedance IPTdwn is set to the normal temperature corresponding impedance, the real element temperature TRdwn of the downstream side air-fuel ratio sensor 41 gradually rises, and along with this, the real impedance IPRdwn of the downstream side air-fuel ratio sensor 41 gradually drops.

Moreover, the temperature Tw of the engine cooling water also rises along with an elapsed time from the start of the internal combustion engine. In the example as shown in FIG. 12, at a time $t_4$, the temperature Tw of the engine cooling water becomes one equal to or larger than a reference water temperature Twref.

The reference water temperature Twref is briefly described herein. As conditions for carrying out the abnormality diagnosis control of the downstream side air-fuel ratio sensor 41, various conditions can be listed. To be specific, the conditions for carrying out the abnormality diagnosis control are satisfied, when the fuel cut-off control is carried out, the temperature Tw of the engine cooling water is equal to or larger than a lower limit water temperature, no abnormality such as a reduced or disconnected voltage of a storage battery is detected, an external atmospheric pressure is equal to or larger than a prescribed pressure lower than a standard atmospheric pressure and the like. It is judged whether or not the abnormality of the voltage of the storage battery and the like and a condition associated with the external atmospheric pressure are satisfied while the engine is started, and in contrast, with respect to a satisfaction of a condition associated with the temperature Tw of the engine cooling water, a time to an extent is required from the start of the engine. Accordingly, if the condition for carrying out the fuel cut-off control is excluded, the condition associated with the temperature Tw of the engine cooling water can be said to be a condition that is satisfied at latest after the start of the engine. That is, if the abnormality of the voltage of the storage battery and the like or the condition associated with the external atmospheric pressure is satisfied, when the temperature Tw of the engine cooling water becomes one equal to or larger than the lower limit water temperature, the conditions for carrying out the abnormality diagnosis control other than the condition for carrying out the fuel cut-off control are satisfied.

Moreover, in the embodiment, at a time $t_4$, when the temperature Tw of the engine cooling water becomes one the same as the lower limit water temperature or equal to or larger than the reference water temperature Twref lower than the lower limit water temperature, the target element temperature TTdwn is set to the high set temperature. Along with this, the target impedance IPTdwn is set to the high temperature corresponding impedance corresponding to the high set temperature. When the target impedance IPTdwn is set to the high temperature corresponding impedance, the real element temperature TRdwn of the downstream side air-fuel ratio sensor 41 rises towards the high set temperature, and along with this, the real impedance IPRdwn of the downstream side air-fuel ratio sensor 41 gradually drops.

In this way, in the embodiment, after the internal combustion engine is started and when the temperature Tex of the exhaust pipe 22 around the downstream side air-fuel ratio sensor 41 becomes one equal to or larger than the reference pipe temperature Texref, the heating based on the heating portion 56 is begun. The target element temperature TTdwn at this time is set to a normal target element temperature. Then, when the temperature Tw of the engine cooling water becomes one equal to or larger than the reference water temperature, the target element temperature TTdwn is set to the high set temperature higher than the normal one. Accordingly, according to the embodiment, a time when the temperature of the downstream side air-fuel ratio sensor 41 rises to the high set temperature can be delayed to one before the conditions for carrying out the abnormality diagnosis control other than the condition for carrying out the fuel cut-off control are satisfied or are to be satisfied. As a result, the consumed electric power along with the heating of the downstream side air-fuel ratio sensor 41 can be suppressed to a comparatively small amount.

It should be noted that in the above embodiment, when the temperature of the engine cooling water becomes one equal to or larger than the reference pipe temperature, the target element temperature is made to rise, and the target impedance is made to drop. However, the rise of the target element temperature is allowed as long as the conditions for carrying out the abnormality diagnosis control other than the condition for carrying out the fuel cut-off control are satisfied, and not necessarily when the temperature of the engine cooling water becomes one equal to or larger than the reference pipe temperature. For example, one of the conditions for carrying out the abnormality diagnosis control includes an oil temperature of lubricating oil circulating in the internal combustion engine becoming one equal to or larger than a specified temperature, and the target element temperature is made to rise when the oil temperature of the lubricating oil becomes one equal to or larger than the prescribed temperature in the case where the above condition other than the condition for carrying out the fuel cut-off control is satisfied at latest.

Figure 13:
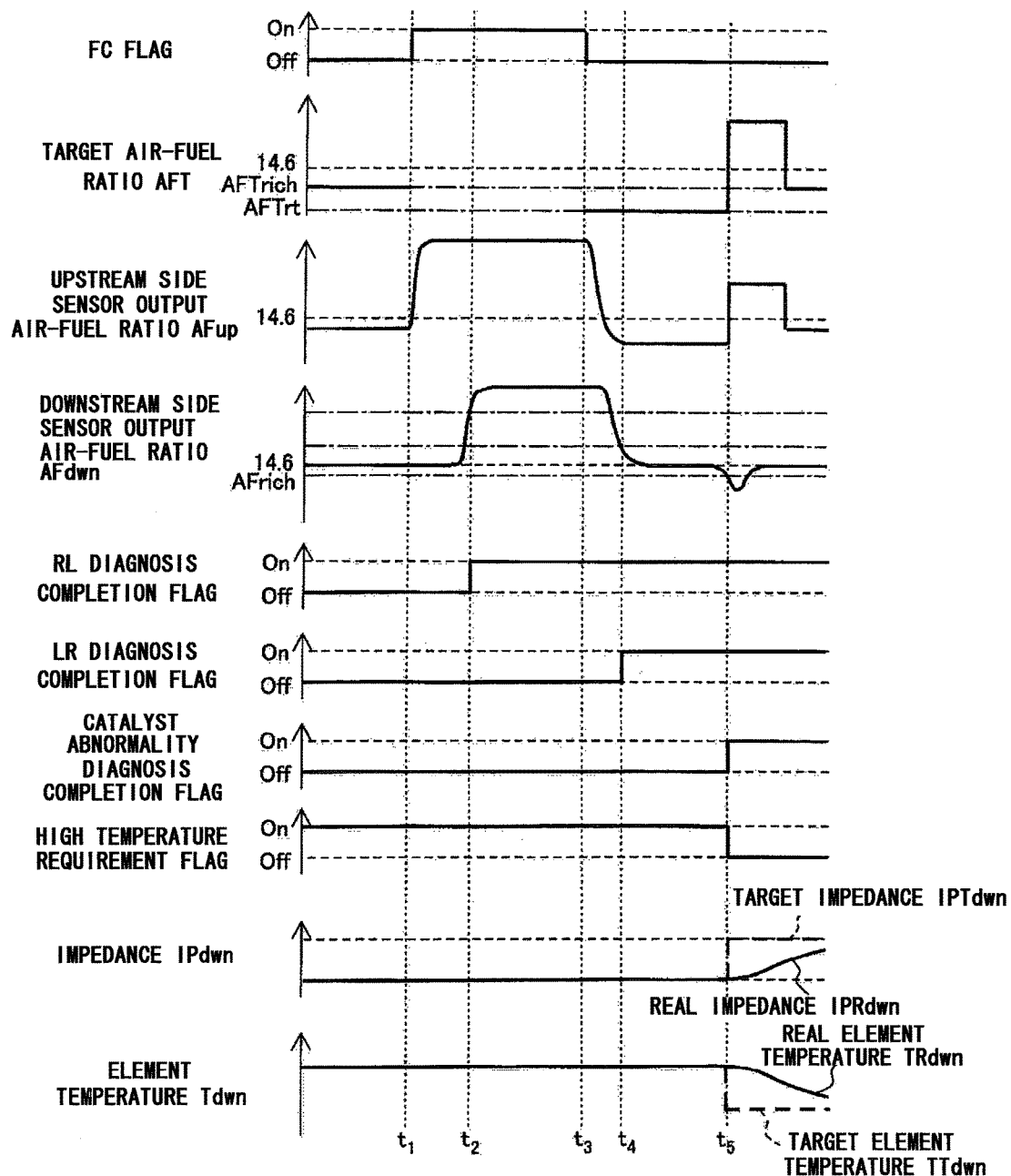
FIG. 13 is a time chart showing the target air-fuel ratio and the like when the fuel cut-off control is performed, which is similar to FIG. 9.

FIG. 13 is a time chart showing the target air-fuel ratio and the like in an initial fuel cut-off control after the engine is started, which is similar to FIG. 9. In the example as shown in FIG. 13, at a time $t_1$, the fuel cut-off control is begun. Along with this, the output air-fuel ratio AFup of the upstream side air-fuel ratio sensor 40 rises sharply, and then the output air-fuel ratio AFdwn of the downstream side air-fuel ratio sensor 41 rises sharply. At this time, the abnormality diagnosis of the downstream side air-fuel ratio sensor 41 is performed, and at a time $t_2$ when the abnormality diagnosis is completed, the RL diagnosis completion flag is set to ON. Then, at a time $t_3$, the fuel cut-off control is completed. Along with this, the output air-fuel ratio AFup of the upstream side air-fuel ratio sensor 40 drops sharply, and then the output air-fuel ratio AFdwn of the downstream side air-fuel ratio sensor 41 also drops. In the meanwhile, the abnormality diagnosis of the downstream side air-fuel ratio sensor 41 is performed, and at a time $t_4$ when the abnormality diagnosis is completed, the LR diagnosis completion flag is set to ON.

Accordingly, in the example as shown in FIG. 9, at a time $t_4$, the abnormality diagnosis of the downstream side air-fuel ratio sensor 41 performed during the fuel cut-off control is wholly completed. However, in the present embodiment, at the time $t_4$, the target element temperature TTdwn of the downstream side air-fuel ratio sensor 41 does not drop to the low set temperature, but is still maintained as the high set temperature. Accordingly, the target impedance IPTdwn of the downstream side air-fuel ratio sensor 41 is also maintained comparatively low.

After the completion of the fuel cut-off control, when the target air-fuel ratio AFT is set to the after-restoration rich air-fuel ratio AFTrt, the oxygen absorption amount OSA of the downstream side exhaust purification catalyst 24 decreases to substantially zero, and along with this, the output air-fuel ratio AFdwn of the downstream side air-fuel ratio sensor 41 drops to one below the rich set air-fuel ratio AFrich. In the present embodiment, when the output air-fuel ratio AFdwn drops to one below the rich set air-fuel ratio AFrich, the target impedance IPTdwn of the downstream side air-fuel ratio sensor 41 rises from the high temperature corresponding impedance to the normal temperature corresponding impedance. That is, the target element temperature TTdwn of the downstream side air-fuel ratio sensor 41 drops from the high set temperature to the low set temperature. Along with this, after a time $t_5$, the real element temperature TRdwn of the downstream side air-fuel ratio sensor 41 gradually drops, and is converged at the low set temperature after a short while. Accordingly, after the time $t_5$, the real impedance IPTdwn of the downstream side air-fuel ratio sensor 41 gradually rises, and is converged at the normal temperature corresponding impedance after a short while.

In this way, in the present embodiment, the result of performing the after-restoration richness control after the fuel cut-off control is that the target element temperature TTdwn is set to a temperature higher than the normal one, till the output air-fuel ratio AFdwn of the downstream side air-fuel ratio sensor 41 drops to one below the rich judgment air-fuel ratio AFrich. The contents below describe advantages of the target element temperature TTdwn set in this manner.

When the after-restoration richness control is performed after the fuel cut-off control, as shown in FIG. 6, the oxygen absorption amount of the upstream side exhaust purification catalyst 20 gradually decreases from the maximum oxygen absorbability amount Cmax. Moreover, when the oxygen absorption amount of the upstream side exhaust purification catalyst 20 becomes substantially zero, the output air-fuel ratio AFdwn of the downstream side air-fuel ratio sensor 41 reaches the rich judgment air-fuel ratio AFrich. Accordingly, an accumulative amount of excess oxygen (hereinafter referred to as an "accumulative oxygen excess amount") flowing into the upstream side exhaust purification catalyst 20 from the beginning of the after-restoration richness control to the output air-fuel ratio AFdwn of the downstream side air-fuel ratio sensor 41 becoming one below the rich judgment air-fuel ratio AFrich corresponds to the maximum oxygen absorbability amount Cmax of the upstream side exhaust purification catalyst 20. It should be noted that the excess oxygen flowing into the upstream side exhaust purification catalyst 20 refers to an excess oxygen amount when the air-fuel ratio of the exhaust gas flowing into the upstream side exhaust purification catalyst 20 is to be made to become the theoretical air-fuel ratio.

Herein, generally in an exhaust purification catalyst having an oxygen absorption capacity, when its deterioration degree is large, the maximum oxygen absorbability amount Cmax is reduced. Accordingly, the deterioration degree of the exhaust purification catalyst can be monitored by detecting the maximum oxygen absorbability amount Cmax. Accordingly, the deterioration degree of the exhaust purification catalyst can be detected by calculating the accumulative oxygen excess amount during the after-restoration richness control.

However, during the after-restoration richness control, when the real element temperature TRdwn of the downstream side air-fuel ratio sensor 41 changes, the output air-fuel ratio AFdwn of the downstream side air-fuel ratio sensor 41 will sometimes become unstable along therewith. As a result, although the oxygen of an amount to an extent is actually absorbed in the upstream side exhaust purification catalyst 20, a case that the output air-fuel ratio AFdwn of the downstream side air-fuel ratio sensor 41 becomes one below the rich judgment air-fuel ratio also exists. In this case, the deterioration degree of the upstream side exhaust purification catalyst 20 cannot be accurately detected. With respect this point, in the present embodiment, the real element temperature TRdwn of the downstream side air-fuel ratio sensor 41 is still maintained high and constant, till the output air-fuel ratio AFdwn of the downstream side air-fuel ratio sensor 41 becomes one below the rich judgment air-fuel ratio. Accordingly, the deterioration degree of the upstream side exhaust purification catalyst 20 can be accurately detected.

It should be noted that in the present embodiment, the diagnosis of the deterioration degree of the upstream side exhaust purification catalyst 20, i.e., the abnormality diagnosis, is performed during the after-restoration richness control. To be specific, the abnormality diagnosis of the upstream side exhaust purification catalyst 20 is performed from the time $t_3$ when the after-restoration richness control begins to the time $t_5$ when the output air-fuel ratio AFdwn of the downstream side air-fuel ratio sensor 41 becomes one below the rich set air-fuel ratio. Accordingly, as shown in FIG. 13, at the time $t_5$, a catalyst abnormality completion flag is set to ON, and along with this, the target element temperature TTdwn of the downstream side air-fuel ratio sensor 41 drops from the high set temperature to the low set temperature.

<Flow Chart>

Figure 14:
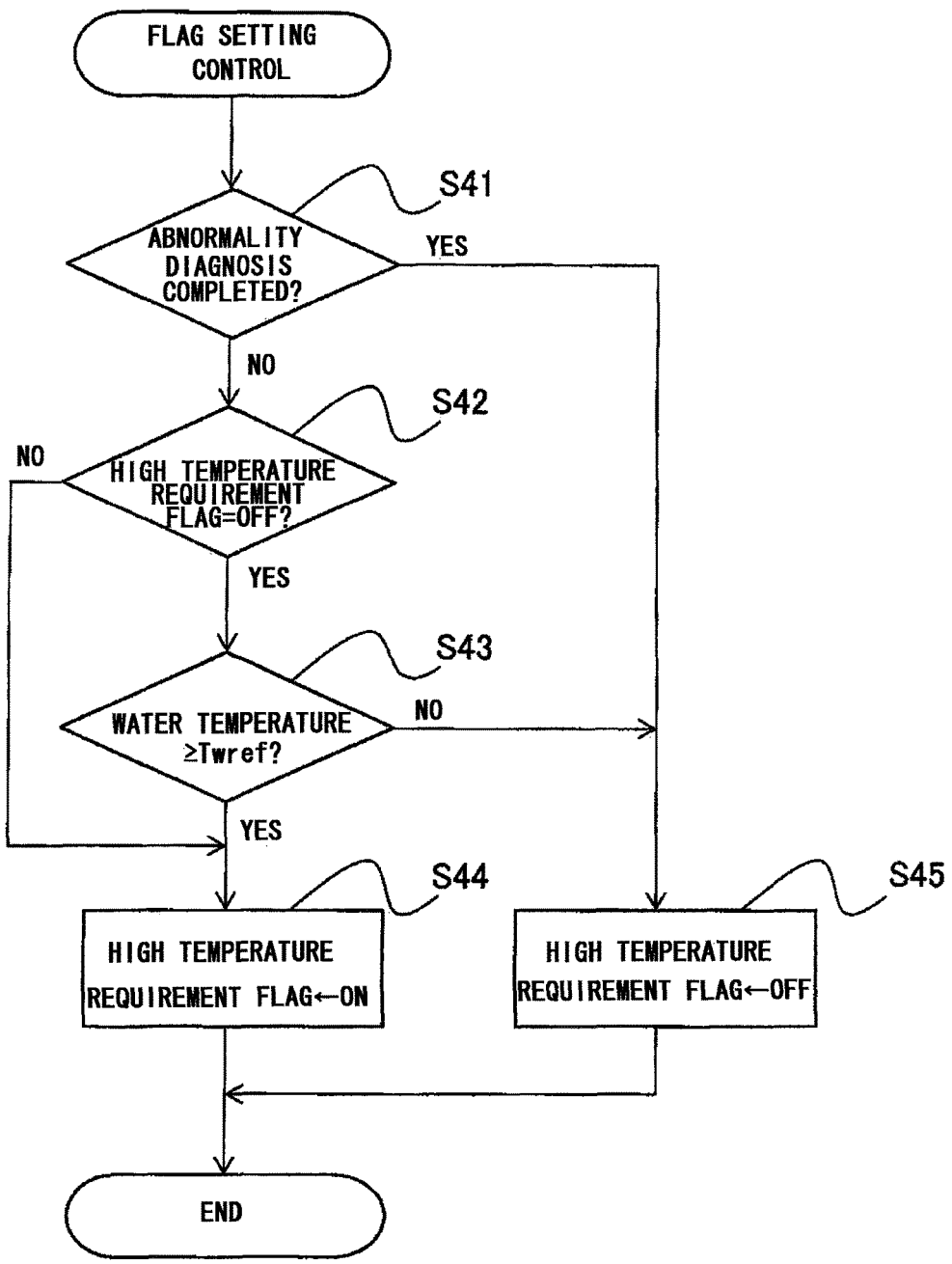
FIG. 14 is a flow chart showing a control routine of the setting control of the high temperature requirement flag.

FIG. 14 is a flow chart showing a control routine of a setting control of the high temperature requirement flag. The control routine as shown in FIG. 14 is performed at an interval of time.

As shown in FIG. 14, firstly in a step S41, it is judged whether or not the abnormality diagnosis is completed. Herein, the abnormality diagnosis not only means the abnormality diagnosis of the downstream side air-fuel ratio sensor 41, but also means the abnormality diagnosis of the upstream side exhaust purification catalyst 20. Accordingly, in the step S41, when both of the abnormality diagnosis of the downstream side air-fuel ratio sensor 41 and the abnormality diagnosis of the upstream side exhaust purification catalyst 20 are completed, it is judged that the abnormality diagnosis is completed. On the other hand, when neither or only one of the abnormality diagnosis of the downstream side air-fuel ratio sensor 41 and the abnormality diagnosis of the upstream side exhaust purification catalyst 20 is completed, it is judged that the abnormality diagnosis has not been completed. In the step S41, a step S42 is entered, in the case where it is judged that the abnormality diagnosis has not been completed.

In the step S42, it is judged whether or not the high temperature requirement flag is OFF. In the case where it is judged that the high temperature requirement flag is OFF for the reason that the engine is just started or the like, a step S43 is entered. In the step S43, it is judged whether or not the temperature Tw of the engine cooling water is equal to or larger than the reference water temperature Twref. In the case where it is judged that the temperature Tw of the engine cooling water is lower than the reference water temperature Twref for the reason that the time has not elapsed much from a cold start of the internal combustion engine, a step S45 is entered. In the step S45, the high temperature requirement flag is still set to OFF, and the control routine is completed. On the other hand, in the case where it is judged in the step S43 that the temperature Tw of the engine cooling water is equal to or larger than the reference water temperature Twref, a step S44 is entered. In the step S44, the high temperature requirement flag is set to ON, and the control routine is completed.

When the high temperature requirement flag is set to ON, in the following control routine, it is judged in the step S42 that the high temperature requirement flag does not become OFF, and the step S43 is skipped. Accordingly, the step S44 is entered from the step S42, and the high temperature requirement flag is continued to be set to ON.

Then, when the abnormality diagnosis of the downstream side air-fuel ratio sensor 41 and the abnormality diagnosis of the upstream side exhaust purification catalyst 20 are completed, the step S45 is entered from the step S41, and the high temperature requirement flag is set to OFF. Herein, in the present embodiment, the fuel cut-off control and the after-restoration richness control are performed after the start of the engine, and thereafter, when the output air-fuel ratio AFdwn of the downstream side air-fuel ratio sensor 41 becomes one below the rich judgment air-fuel ratio AFrich, it is judged that the abnormality diagnosis is completed.

Other Modified Examples

It should be noted that in the first embodiment, when the temperature Tex of the exhaust pipe 22 around the downstream-side air-fuel ratio sensor 41 rises to the reference pipe temperature Texref, the target element temperature of the downstream side air-fuel ratio sensor 41 is set to the high set temperature. Moreover, in the second embodiment, when the conditions for carrying out the abnormality diagnosis control other than the condition for carrying out the fuel cut-off control are satisfied, the target element temperature of the downstream side air-fuel ratio sensor 41 is set to the high set temperature. However, the time for setting the target element temperature of the downstream side air-fuel ratio sensor 41 to the high set temperature is not necessarily limited to these times. Accordingly, for example, a time between these two times is allowed, so it can be said that the setting of the target element temperature of the downstream side air-fuel ratio sensor 41 to the high set temperature is performed at a time when a specified temperature rise begins after the start of the engine.

Moreover, in the first embodiment, when the abnormality diagnosis control of the downstream side air-fuel ratio sensor 41 performed along with the fuel cut-off control is completed, the target element temperature is made to drop from the high set temperature to the normal set temperature. Moreover, in the second embodiment, when the output air-fuel ratio of the downstream side air-fuel ratio sensor 41 after the fuel cut-off control reaches one below the rich judgment air-fuel ratio for the first time, the target element temperature is made to drop from the high set temperature to the low set temperature. However, the time for making the target element temperature of the downstream side air-fuel ratio sensor 41 drop from the high set temperature to the low set temperature is not necessarily limited to these times. Accordingly, for example, a time between these two times is allowed.

Alternatively, in the internal combustion engine where the abnormality diagnosis of the upstream side exhaust purification catalyst 20 is performed independently of the fuel cut-off control, the drop of the target element temperature can be waited for, till such an abnormality diagnosis of the upstream side exhaust purification catalyst 20 is completed. The reason is that the higher the element temperature of the downstream side air-fuel ratio sensor 41 is, the higher a detection speed (responsibility) of the air-fuel ratio is, so the accuracy of the abnormality diagnosis of the upstream side exhaust purification catalyst 20 can be improved by setting the target element temperature in this manner. As mentioned above, it can be said that making the target element temperature of the downstream side air-fuel ratio sensor 41 drop from the high set temperature to the low set temperature is performed at a time when the prescribed temperature rise is completed after the abnormality diagnosis control of the downstream side air-fuel ratio sensor 41 using the fuel cut-off control is completed.

Moreover, in the above embodiments, the cup-shaped air-fuel ratio sensor as shown in FIG. 2 is used as the air-fuel ratio sensor. The reason is that as compared with a laminated air-fuel ratio sensor, the cup-shaped air-fuel ratio sensor has an excellent water resistance, and the output is large, so the detection accuracy of the air-fuel ratio is high.

Herein, in the cup-shaped air-fuel ratio sensor, as compared with the laminated air-fuel ratio sensor, the obtained applied voltage in the limit current area rises with respect to the exhaust gas of the same air-fuel ratio. Accordingly, in the cup-shaped air-fuel ratio sensor, as compared with the laminated air-fuel ratio sensor, the obtained applied voltage in the limit current area with respect to the atmospheric gas rises. That is, in the cup-shaped air-fuel ratio sensor, as compared with the laminated air-fuel ratio sensor, a trend as shown in FIG. 7 becomes large. Accordingly, when the cup-shaped air-fuel ratio sensor is used, an accuracy drop of the abnormality diagnosis can be suppressed more efficiency by performing the temperature control of the air-fuel ratio sensor as described above. However, since an efficient effect also exists with respect to the laminated air-fuel ratio sensor, the laminated air-fuel ratio sensor can be also used as the air-fuel ratio sensor.

What is claimed is:

1. A control device of an internal combustion engine, the internal combustion engine comprising an air-fuel ratio sensor provided on an exhaust passage of the internal combustion engine, the air-fuel ratio sensor having a heating device for heating an element of the air-fuel ratio sensor, the control device comprising
an electronic control unit configured to:
carry out a fuel cut-off control and an abnormality diagnosis control, the fuel cut-off control being a control that stops or reduces a fuel supply to a combustion chamber of the internal combustion engine during an operation of the internal combustion engine, and the abnormality diagnosis control being a control that performs an abnormality diagnosis of the air-fuel ratio sensor during the fuel cut-off control or after completion of the fuel cut-off control;
control the heating device to make an element temperature of the air-fuel ratio sensor become a target element temperature; and
set the target element temperature of the air-fuel ratio sensor during a high temperature control period from a time when a prescribed high temperature control begins after a start of the internal combustion engine to a time when the prescribed high temperature control is completed after completion of the abnormality diagnosis control of the air-fuel ratio sensor to be higher than the target element temperature outside the high temperature control period.

2. The control device of the internal combustion engine according to claim 1, wherein
the electronic control unit is configured to begin carrying out the abnormality diagnosis control when conditions for carrying out the abnormality diagnosis including a condition for carrying out the fuel cut-off control are satisfied, and
the time when the high temperature control begins is a time when or before the conditions for carrying out the abnormality diagnosis other than the condition for carrying out the fuel cut-off control are satisfied.

3. The control device of the internal combustion engine according to claim 1, wherein the target element temperature during the high temperature control period is a temperature at which the air-fuel ratio sensor outputs a limit current when an atmospheric gas circulates around the air-fuel ratio sensor.

4. The control device of the internal combustion engine according to claim 1, wherein the air-fuel ratio sensor is a cup-shaped air-fuel ratio sensor.

5. The control device of the internal combustion engine according to claim 1, wherein the air-fuel ratio sensor is a downstream side air-fuel ratio sensor, the air-fuel ratio sensor is provided on a downstream side of an exhaust flow direction of an exhaust purification catalyst provided on the exhaust passage of the internal combustion engine.

6. The control device of the internal combustion engine according to claim 1, wherein
the electronic control unit is configured to carry out a catalyst abnormality diagnosis control, the catalyst abnormality diagnosis control is a control that performs an abnormality diagnosis of an exhaust purification catalyst provided on the exhaust passage of the internal combustion engine after the completion of the fuel cut-off control, and
in a case where a time when the catalyst abnormality diagnosis control of the exhaust purification catalyst is completed is later than a time when the abnormality diagnosis control of the air-fuel ratio sensor is completed,
the time when the high temperature control is completed is a time after the abnormality diagnosis control of the exhaust purification catalyst is completed.

7. The control device of the internal combustion engine according to claim 1, wherein:
the electronic control unit is configured to carry out a catalyst abnormality diagnosis control, the catalyst abnormality diagnosis control is a control that performs an abnormality diagnosis of an exhaust purification catalyst provided on the exhaust passage of the internal combustion engine after the completion of the fuel cut-off control;
the electronic control unit is configured to perform an after-restoration richness control, the after-restoration richness control is a control that controls an air-fuel ratio by making an air-fuel ratio of an exhaust gas flowing into the exhaust purification catalyst provided on the exhaust passage of the internal combustion engine become a rich air-fuel ratio richer than a theoretical air-fuel ratio, after the completion of the fuel cut-off control; and
the time when the high temperature control is completed is a time when or before the after-restoration richness control is completed.

8. A control method of an internal combustion engine, the internal combustion engine comprising an air-fuel ratio sensor provided on an exhaust passage of the internal combustion engine, the air-fuel ratio sensor having a heating device for heating an element of the air-fuel ratio sensor, and the internal combustion engine is controlled by an electronic control unit, the control method comprising:
carrying out, by the electronic control unit, a fuel cut-off control and an abnormality diagnosis control, the fuel cut-off control being a control that stops or reduces a fuel supply to a combustion chamber of the internal combustion engine during an operation of the internal combustion engine, and the abnormality diagnosis control being a control that performs an abnormality diagnosis of the air-fuel ratio sensor during the fuel cut-off control or after completion of the fuel cut-off control;
controlling, by the electronic control unit, the heating device to make an element temperature of the air-fuel ratio sensor become a target element temperature; and
setting, by the electronic control unit, the target element temperature of the air-fuel ratio sensor during a high temperature control period from a time when a prescribed high temperature control begins after a start of the internal combustion engine to a time when the prescribed high temperature control is completed after completion of the abnormality diagnosis control of the air-fuel ratio sensor to be higher than the target element temperature outside the high temperature control period.

* * * * *